US009002455B2

(12) United States Patent  (10) Patent No.: US 9,002,455 B2
Hellman et al.  (45) Date of Patent: Apr. 7, 2015

(54) SYSTEMS AND METHODS FOR ASSESSING AND EXPLOITING CONCURRENT CATHODAL AND ANODAL CAPTURE USING AN IMPLANTABLE MEDICAL DEVICE

(75) Inventors: Heidi Hellman, Los Angeles, CA (US); Kyungmoo Ryu, Palmdale, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 13/351,958

(22) Filed: Jan. 17, 2012

(65) Prior Publication Data

US 2013/0184777 A1  Jul. 18, 2013

(51) Int. Cl.
*A61N 1/18* (2006.01)
*A61B 5/0452* (2006.01)
*A61N 1/37* (2006.01)
*A61B 5/042* (2006.01)
*A61B 5/00* (2006.01)

(52) U.S. Cl.
CPC ............... *A61N 1/3712* (2013.01); *A61B 5/042* (2013.01); *A61B 5/0452* (2013.01); *A61B 5/7242* (2013.01)

(58) Field of Classification Search
None
See application file for complete search history.

(56) References Cited

U.S. PATENT DOCUMENTS

| | | |
|---|---|---|
| 4,858,610 A | 8/1989 | Callaghan et al. |
| 5,417,718 A | 5/1995 | Kleks et al. |
| 6,687,545 B1 * | 2/2004 | Lu .................................... 607/28 |
| 7,440,800 B2 | 10/2008 | Mower |
| 7,706,865 B1 | 4/2010 | Snell |
| 7,899,536 B1 | 3/2011 | Hellman |
| 2004/0064162 A1 * | 4/2004 | Manrodt et al. ................. 607/28 |
| 2009/0240298 A1 | 9/2009 | Lian et al. |
| 2009/0270938 A1 * | 10/2009 | Pei et al. ......................... 607/28 |
| 2010/0042176 A1 | 2/2010 | Snell |
| 2010/0121396 A1 * | 5/2010 | Gill et al. ......................... 607/17 |
| 2010/0305644 A1 * | 12/2010 | Spinelli et al. ................. 607/17 |
| 2010/0331921 A1 * | 12/2010 | Bornzin et al. ................. 607/62 |
| 2011/0196442 A1 * | 8/2011 | Ryu et al. ........................ 607/17 |

* cited by examiner

*Primary Examiner* — Brian T Gedeon
*Assistant Examiner* — Ankit Tejani

(57) ABSTRACT

Techniques are provided for use by an implantable medical device for assessing and controlling concurrent anodal/cathodal capture. In one example, the device delivers bipolar pacing stimulus while sensing a bipolar intracardiac electrogram (IEGM) and while adjusting a magnitude of the pacing stimulus. The device analyzes the bipolar IEGM signals to detect an indication of activation representative of concurrent anodal and cathodal capture. Preferably, the pulse magnitude is set relative to the anodal/cathodal capture threshold based upon clinician programming in response to the needs of the patient. In this manner, concurrent anodal and cathodal capture can be selectively activated or deactivated based on clinician instructions received from a device programmer or other external programming device. Techniques exploiting both bipolar and unipolar IEGM signals to assess and control concurrent anodal/cathodal capture are also described. Techniques for use with quad-pole leads to achieve dual-site or quad-site capture are also set forth.

22 Claims, 17 Drawing Sheets

SYSTEMS AND METHODS FOR ASSESSING AND EXPLOITING CONCURRENT CATHODAL AND ANODAL CAPTURE USING AN IMPLANTABLE MEDICAL DEVICE

FIELD OF THE INVENTION

The invention generally relates to implantable cardiac stimulation devices such as pacemakers, implantable cardioverter-defibrillators (ICDs) and cardiac resynchronization therapy (CRT) devices and, in particular, to techniques for controlling cathodal and anodal capture delivered by an implantable medical device, particularly devices equipped for multi-site left ventricular (MSLV) pacing.

BACKGROUND OF THE INVENTION

A pacemaker is a medical device for implant within a patient that provides electrical stimulation pulses to selected chambers of the heart. Such stimulation pulses cause the muscle tissue of the heart (myocardial tissue) to depolarize and contract, thereby causing the heart to beat at a controlled rate. Most pacemakers can be programmed to operate in a demand mode of operation, i.e., to generate and deliver stimulation pulses to the heart only when the heart fails to beat on its own. To this end, the pacemaker senses cardiac activity, i.e., heart beats, and if the heart beats do not occur at a prescribed rate, stimulation pulses are generated and delivered to an appropriate heart chamber to force the heart to beat.

Proper operation of a pacemaker presupposes that stimulation pulses generated by the pacemaker effectuate capture. Capture refers to the ability of a given stimulation pulse generated by a pacemaker to cause depolarization of nearby myocardial tissues, i.e., to generate an evoked response (ER) and to cause heart muscle to contract. Failure of a pulse to effectuate capture (i.e. no response is evoked) is referred to as a "loss of capture" or LOC. While many factors influence whether a given stimulation pulse effectuates capture, a principal factor is the energy of the stimulation pulse. The energy of the stimulation pulse, in turn, is determined by the amplitude and width (or duration) of the stimulation pulse generated by the pacemaker and the electrical resistance of the pacemaker system/tissue interface circuit. Advantageously, in a programmable pacemaker, both the amplitude and pulse width of the stimulation pulse are parameters that may be programmably controlled or set to a desired value. Herein, the term "magnitude" is used to generally refer to the energy of pulse. Magnitude may be adjusted by changing either or both pulse amplitude or pulse width.

Stimulation pulses may be delivered either in a bipolar mode or a unipolar mode. The term "bipolar" is used herein to refer to a mode wherein both of the electrodes used to deliver the stimulation (or sense cardiac signals) are located on or in the heart of the patient. One of the electrodes is used as a cathode (negative pole) and the other is used as an anode (positive pole). In some cases, both the cathodal and anodal electrodes are located on or within the same heart chambers, such as the left ventricle (LV). In other cases, the two electrodes of the bipolar pair are located on or within different chambers. For example, the cathode may be on the LV, whereas the anode may be in the right ventricle (RV). This type of bipolar stimulation can also be referred to as cross-chamber stimulation. The term "unipolar" is used herein to refer to a mode wherein only one of the electrodes used to deliver the stimulation (or sense cardiac signals) is located on or in the heart of the patient. This electrode is usually the cathode. The device housing or "can" is used as the other electrode (typically the anode.) Note that, in the literature, cross-chamber forms of stimulation/sensing are sometimes referred to as "unipolar" but, to avoid confusion herein, unipolar is reserved for stimulation/sensing modes where only one of the electrodes is located on or in the heart.

Conventionally, bipolar stimulation pulses are set to a magnitude sufficient to effectuate capture only at the cathode (negative pole) of the pair of electrodes used to deliver the stimulus. This is referred to herein as "cathodal-only" stimulation. A higher pulse magnitude is typically required to additionally effectuate capture at the anode (positive pole) of the electrode pair. This is referred to herein as "anodal/cathodal" stimulation. Usually, anodal/cathodal stimulation is not warranted, and the additional energy required to achieve anodal capture as well as cathodal capture would unnecessarily burden the energy resources of the device, possibly reducing battery life. However, concurrent anodal/cathodal capture may be desirable in some cases since it achieves capture at two separate sites within the heart and hence may achieve synchronized myocardial contractions at two locations.

Many pacemakers now include automatic stimulation threshold search systems that, following implant of the pacemaker, automatically determine a capture threshold and set the stimulation pulse amplitude accordingly, but these systems typically apply only to cathodal stimulation, i.e. the capture threshold is the threshold for cathodal-only stimulation. Herein, the capture threshold (or minimum pulse energy) sufficient to evoke cathodal capture only is abbreviated $CAP_{CATHODE}$. Likewise, many pacemakers include automatic capture verification systems which, following delivery of stimulation pulses, automatically verifies that the pulses are captured (i.e. an ER is produced) and takes steps if capture is lost, but these systems also typically apply only to cathodal stimulation.

It would be desirable to provide improved techniques for determining capture thresholds and verifying capture that additionally apply to concurrent anodal/cathodal capture. Aspects of the present invention are directed to this end. For background regarding anodal capture, see, e.g. techniques described in U.S. Patent Application 2010/0121396 of Gill et al., entitled "Enhanced Hemodynamics through Energy-Efficient Anodal Pacing" and U.S. patent application Ser. No. 11/961,720, filed Dec. 20, 2007, of Snell et al., entitled "Method and Apparatus with Anodal Capture Monitoring."

Other aspects of the present invention are directed to exploiting concurrent anodal/cathodal stimulation techniques for use with MSLV pacing. MSLV pacing aims to improve intra-LV synchrony and overall response to CRT by initiating a linear waveform of depolarization using the various electrodes of a multi-polar LV lead. State-of-the-art CRT devices typically offer two independent LV pulses (LV1 and LV2) to capture two LV electrode locations (i.e., dual-site capture) using cathodal capture. For example, when using a quad-pole LV lead having a distal tip electrode (D1), a first intermediate ring electrode (M2), a second intermediate ring electrode (M3) and a proximal ring electrode (P4), the first LV pulse (LV1) may be delivered using D1-M2 to achieve cathodal capture at D1 while the second LV pulse (LV2) is delivered using P4-M3 to achieve cathodal capture at P4. This requires two pulses to achieve dual-site capture. Within such devices, to achieve capture at all four sites via cathodal-only capture would require delivering a second set of LV1 and LV2 pulses configured to achieve capture at the other two sites (M2 and M3.) This requires more energy and results in an inevitable delay between the first two LV1 and LV2 pulses and the second two LV1 and LV2 pulses, preventing simultaneous or concurrent stimulation at all four sites.

An alternative technique for achieving dual-site capture would instead utilize a single pulse set to a higher magnitude sufficient to achieve both anodal and cathodal capture. For example, a larger magnitude LV1 pulse could be delivered using D1-P4 to achieve cathodal capture at D1 and anodal capture at P4. Depending upon the pulse magnitude, this might be actually consume less energy than using two LV pulses (LV1 and LV2) set for cathodal-only capture. Still further, by exploiting anodal/cathodal capture, stimulation may be delivered at four sites concurrently. For example, a large magnitude LV1 pulse could be delivered using D1-M2 to achieve cathodal capture at D1 and anodal capture at M2 while a large magnitude LV2 pulse could be delivered using M3-P4 to achieve cathodal capture at M3 and anodal capture at P4. Again, depending upon the pulse magnitude, this might be actually consume less energy than using two pairs of pulses—a first LV1, LV2 pair followed closely by a second pair LV1, LV2 pair—set for cathodal-only capture. Whether a reduction in energy consumption can be achieved within a given patient when using concurrent anodal/cathodal stimulation will likely depending on whether the anodal/cathodal capture threshold can be determined precisely and whether concurrent anodal/cathodal capture can be efficiently verified.

Accordingly, it would be desirable to provide improved techniques for determining capture anodal/cathodal thresholds and for verifying anodal/cathodal capture for use with MSLV pacing and various aspects of the invention are directed to this end, as well.

SUMMARY OF THE INVENTION

In an exemplary embodiment, a method is provided for use with an implantable medical device equipped for bipolar electrical stimulation and sensing of heart tissues using cardiac electrodes. Bipolar stimulus is delivered using a pair of the cardiac electrodes while bipolar intracardiac electrogram (IEGM) signals are sensed using the same pair of electrodes. The bipolar IEGM signals are analyzed to detect an indication of evoked responses (ERs) representative of anodal and cathodal capture (with the anodal capture occurring within myocardial tissues associated with an anode of the electrode pair and the cathodal capture occurring within myocardial tissues associated with a cathode of the electrode pair.) An anodal/cathodal capture threshold is then determined that is sufficient to achieve both anodal and cathodal capture, e.g. concurrent anodal/cathodal capture. Thereafter, the magnitude for subsequent stimulus may be set relative to the anodal/cathodal capture threshold to selectively enable or disable concurrent anodal/cathodal capture. Herein, the anodal/cathodal capture threshold is abbreviated as $CAP_{ANODE/CATHODE}$ to distinguish it from the lower cathodal-only capture threshold $CAP_{CATHODE}$.

Preferably, the pulse magnitude is set relative to $CAP_{ANODE/CATHODE}$ based upon clinician programming in response to the needs of the patient. In this manner, concurrent anodal and cathodal capture can be selectively activated or deactivated based on clinician instructions received from a device programmer or other external programming device. As noted above, bipolar stimulus refers to electrical stimulus wherein both the anode and the cathode are implanted on or within the heart. Hence the term as it is used herein encompasses cross-chamber stimulus where, for example, an LV electrode is the cathode and an RV electrode is the anode. The term unipolar stimulus is reserved herein for electrical stimulus where the device housing electrode is used as one of the electrodes (typically the anode.) Herein, "concurrent anodal/cathodal capture" may also be referred to as "concurrent anodal and cathodal capture" or "simultaneous anodal/cathodal capture." It should be understood that, although the terms "concurrent" or "simultaneous" may be used herein, exact or absolute simultaneity is not required and is typically not possible in view of hardware pulse delivery delays, myocardial activation delays, etc. As such, the terms concurrent and simultaneous should be taken to mean "substantially concurrent" and "substantially simultaneous," respectively.

In one example, depending upon device programming, once $CAP_{ANODE/CATHODE}$ is determined, the magnitude for subsequent pacing stimulation is set above $CAP_{ANODE/CATHODE}$ to enable dual-site anodal/cathodal capture to achieve the benefits thereof such as concurrent myocardial activation near both the anodal and cathodal electrodes. In another example, the pulse magnitude is instead set below $CAP_{ANODE/CATHODE}$ to enable single-site cathodal-only capture to gain the benefits thereof such as reduced power consumption. In at least some examples, to detect $CAP_{ANODE/CATHODE}$, the device exploits the observation that, despite the higher pulse magnitudes needed for concurrent anodal and cathodal capture, the resulting ERs within the bipolar IEGM are of lower magnitude. As such, in one example, $CAP_{ANODE/CATHODE}$ is detected by incrementing the magnitude of bipolar pacing stimulus from a predetermined cathodal-only capture threshold ($CAP_{CATHODE}$) to detect the onset of low magnitude ERs within the bipolar IEGM that are representative of concurrent anodal/cathodal capture, i.e. the device detects the sharp drop in the magnitude of ERs within the bipolar IEGM when transitioning from cathodal-only capture to concurrent anodal/cathodal capture. $CAP_{ANODE/CATHODE}$ is then determined to be the pulse magnitude above which the ER within the bipolar IEGM decreases significantly from a relatively high ER associated with cathodal-only capture to a relatively low ER associated with anodal/cathodal capture. Thereafter, concurrent anodal/cathodal capture can be verified by analyzing the bipolar IEGM to detect the presence of relatively low-magnitude ERs (consistent with isoelectric activation within at least some patients), and any loss of concurrent anodal/cathodal capture can be detected and responded to by the device. Loss of capture might occur if the local myocardial tissues are refractory at the time of pulse delivery or if the tissues have changed due to ischemia or other factors.

Note that below the cathodal-only capture threshold ($CAP_{CATHODE}$), ERs are no longer detected within the IEGM at either the anode or cathode, i.e. there is a complete loss of capture. As such, the bipolar IEGM exhibits three distinct capture morphologies: (1) relatively low-magnitude ERs associated with concurrent anodal/cathodal capture; (2) relatively high-magnitude ERs associated with cathodal-only capture (i.e. "regular" cathodal capture with loss of anodal capture); and (3) no ERs associated with pulses at either the anode or cathode (e.g. intrinsic activation following non-capture.) Note that intrinsic activation does not always follow a non-capturing pacing pulse. Indeed, pacemaker dependent patients typically do not have intrinsic activity following non-captured pulses. In some examples, the device thereby exploits the three different morphologies of the bipolar IEGM to detect the $CAP_{ANODE/CATHODE}$ and $CAP_{CATHODE}$ thresholds.

In another example, unipolar IEGMs are additionally sensed, which are compared with bipolar IEGMs to detect the anodal/cathodal capture threshold and to subsequently verify concurrent anodal/cathodal capture. In this regard, a unipolar IEGM derived by using the cathodal electrode of the bipolar electrode pair in combination with the device housing electrode (as the anode), exhibits large ERs regardless of cathodal-only capture or concurrent anodal/cathodal capture.

That is, whereas the bipolar IEGM exhibits three capture morphologies, the unipolar IEGM exhibits only two distinct morphologies: (1) high magnitude ERs associated with capture either at the cathode or at both the anode and cathode; and (2) no ERs associated with no capture at either the anode or cathode. Accordingly, a comparison of the unipolar and bipolar IEGMs at various pulse magnitudes can identify the capture thresholds and verify that the intended form of capture is being achieved (i.e. cathodal-only or concurrent anodal/cathodal capture.) For example, the bipolar IEGM associated with stimulus pulses delivered above $CAP_{ANODE/CATHODE}$ can be compared with the corresponding unipolar IEGM to confirm that the unipolar IEGM exhibits a significantly greater ER than the bipolar IEGM, as expected with concurrent anodal/cathodal capture. If the unipolar IEGM does not exhibit a significantly greater ER than the corresponding bipolar IEGM, then concurrent anodal/cathodal capture is not being achieved and an increase in the pulse magnitude may be required.

In other still examples, the aforementioned concurrent anodal/cathodal capture threshold detection and verification techniques are exploited within systems equipped with a multi-polar LV lead such as a quad-pole LV lead. In one particular example, the device is configured to determine a $CAP_{ANODE/CATHODE}$ value for an LV pair (e.g. D1-P4) such that dual-site LV pacing can be enabled with a single LV pulse (LV1) via concurrent anodal/cathodal stimulation. Preferably, the device also determines the total pulse energy that would otherwise be required to achieve the same dual-site pacing via delivery of two separate cathodal capture-only pulses (LV1, LV2) at the same two sites. The device then chooses the pacing configuration that requires the least energy to achieve the desired dual-site pacing. In yet another example, the device determines a $CAP_{ANODE/CATHODE}$ value for a first LV pair (e.g. D1-M2) and a second $CAP_{ANODE/CATHODE}$ value for a second LV pair (e.g. M3-P4) such that quad-site LV pacing can be selectively enabled with only two pulses (LV1, LV2) via concurrent anodal/cathodal stimulation. Preferably, the device also determines the total pulse energy that would otherwise be required to achieve quad-site pacing via delivery of two separate pairs of cathodal capture-only pulses (delivered in succession) and then chooses the pacing configuration that requires the least energy to achieve the desired quad-site pacing.

Depending upon the particular implementation, these and other techniques may be exploited by the implantable medical device, alone or in combination with a device programmer. For example, the techniques may be performed under clinician supervision during a follow-up session with the patient to select suitable pacing configurations and to set pulse magnitudes to achieve concurrent anodal/cathodal capture. In other examples, the device itself may be programmed to automatically select pacing confirmations and set pulse magnitudes based on the changing needs of the patient—either periodically or as needed—such that direct clinician supervision is not required.

BRIEF DESCRIPTION OF THE DRAWINGS

Features and advantages of the described implementations can be more readily understood by reference to the following description taken in conjunction with the accompanying drawings.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable System

Figure 1:
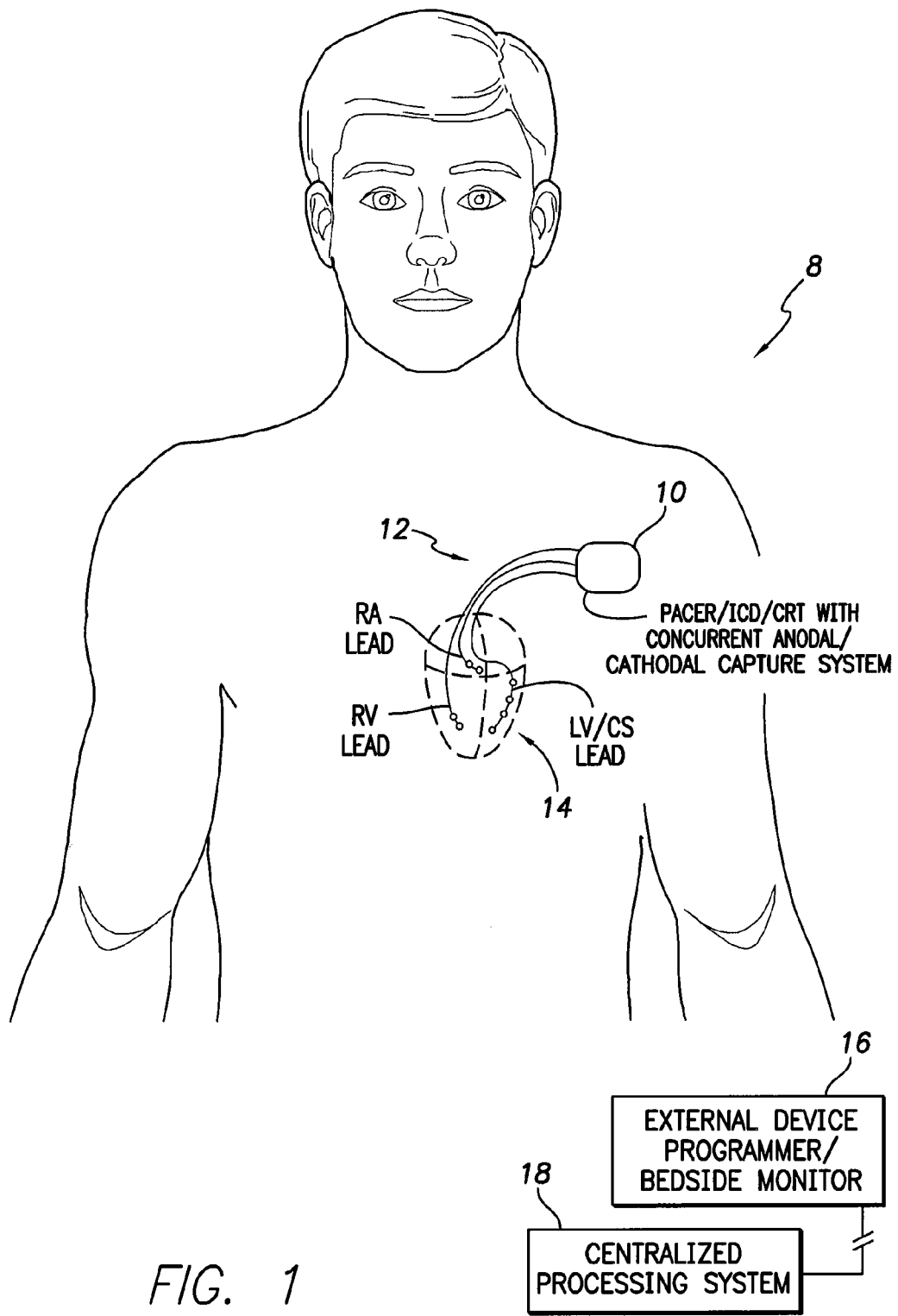
FIG. 1 illustrates components of an implantable medical system having a pacemaker, ICD or CRT device capable of assessing and controlling concurrent anodal/cathodal capture.

FIG. 1 illustrates an implantable medical system 8 capable of assessing and controlling concurrent anodal/cathodal capture using signals sensed bipolar or multi-polar sensing/pacing leads. In this particular example, the implantable medical system 8 includes a pacer/ICD/CRT 10 or other implantable cardiac rhythm management device equipped with a set of cardiac sensing/pacing leads 12 implanted on or within the heart of the patient, including a multi-pole LV lead implanted via the coronary sinus (CS) or great cardiac vein (GCV.) In FIG. 1, a stylized representation of the set of leads is provided. More accurate illustrations of the leads are provided within other figures discussed below. To illustrate the multi-pole configuration of the LV lead, a set of electrodes 14 is shown distributed along the LV lead.

Figure 11:
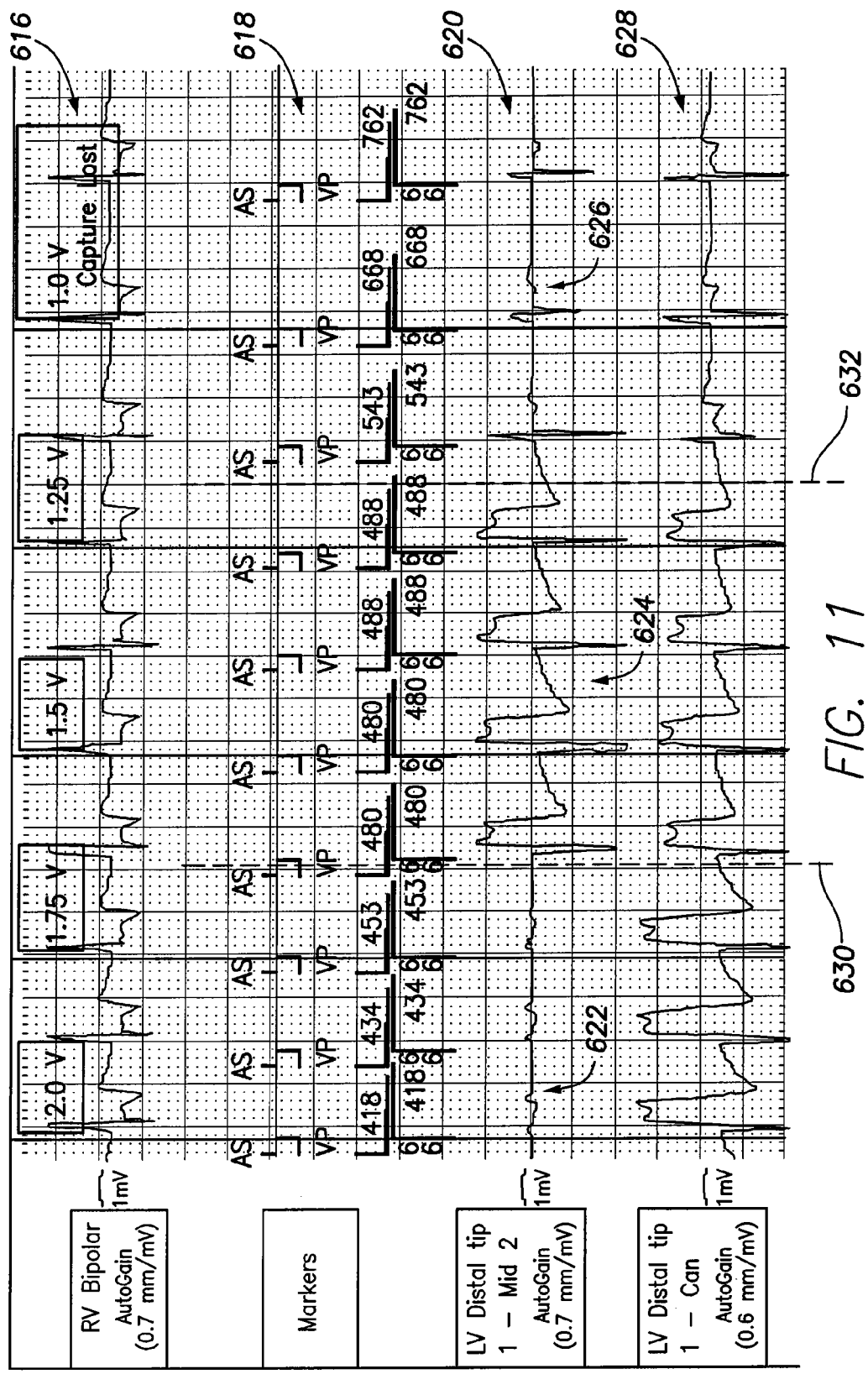
FIG. 11 presents IEGM traces illustrating exemplary bipolar and unipolar IEGM signals exploited by the technique of FIG. 10 to set the concurrent anodal/cathodal capture threshold and subsequently verify capture.

In the examples described herein, a quad-pole (or "quad-rapolar" or "quadripolar") LV lead is employed, such as the QUARTET™ lead provided by St Jude Medical. Herein, the four electrodes of the LV lead are designated as follows: tip (D1), first intermediate ring (M2), second intermediate ring (M3) and proximal ring (P4), as shown in FIG. 11 discussed below. Other suitable leads may instead be employed, including leads with more or fewer electrodes, depending upon the needs of the particular implementation. Also, as shown, an exemplary RV lead is provided that includes a bipolar RV tip/ring electrode pair. An RA lead is also provided that includes a bipolar RA tip/ring pair. Other electrodes of various sizes and shapes may be additionally or alternatively provided, such as various coil electrodes for delivering shock therapy. Although identified as a "pacer/ICD/CRT" in FIG. 1, it should be understood that device 10 can be any suitably-equipped implantable medical device, such as a standalone pacemaker, ICD or CRT device, including CRT-D and CRT-P devices. In the following, for brevity, device 10 will be referred to simply as a pacer/CRT.

Preferably, the pacer/CRT itself assesses and controls concurrent anodal/cathodal capture based on electrocardiac signals (which may also be referred to as cardioelectrical signals) sensed by the leads, such as by performing automated procedures to determine the concurrent anodal/cathodal capture threshold ($CAP_{ANODE/CATHODE}$) and then to verify concurrent anodal/cathodal capture during subsequent pacing. In other implementations, however, the device might additionally or alternatively transmit pertinent electrocardiac parameters to an external device programmer 16, which assesses and controls anodal/cathodal capture based on the parameters under clinician supervision, typically as part of a post-implant follow-up programming session. Note also that other external systems might instead be used such as bedside monitors or the like. In some embodiments, the external system is directly networked with a centralized computing system 18, such as the HOUSECALL™ centralized computing system or the MERLIN@HOME® or MERLIN.NET™ centralized computing systems of St. Jude Medical.

Summary of Concurrent Anodal/Cathodal Capture Techniques

Figure 2:
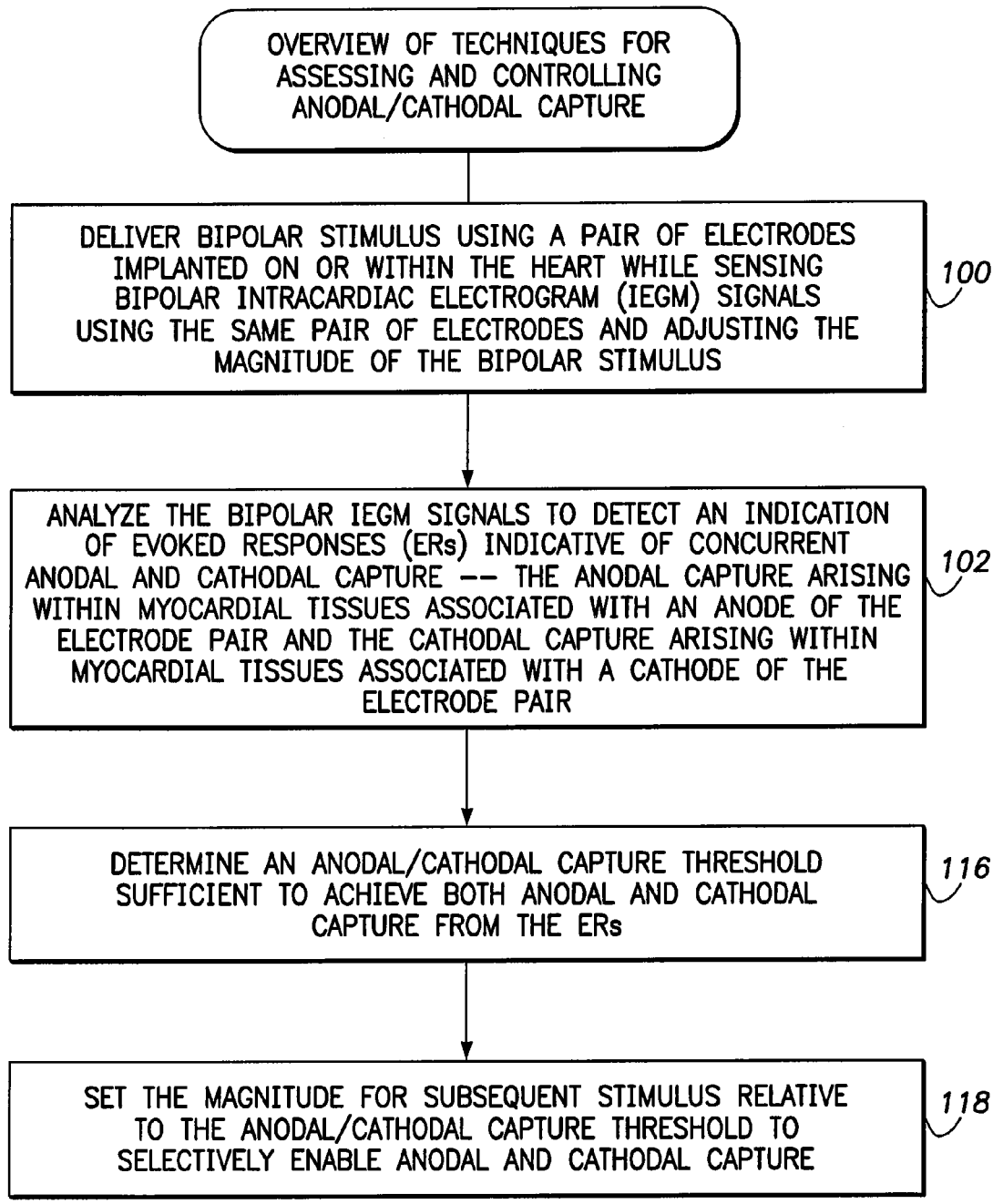
FIG. 2 summarizes the general technique for assessing and controlling concurrent anodal/cathodal capture that may be performed by the system of FIG. 1.
Figure 3:
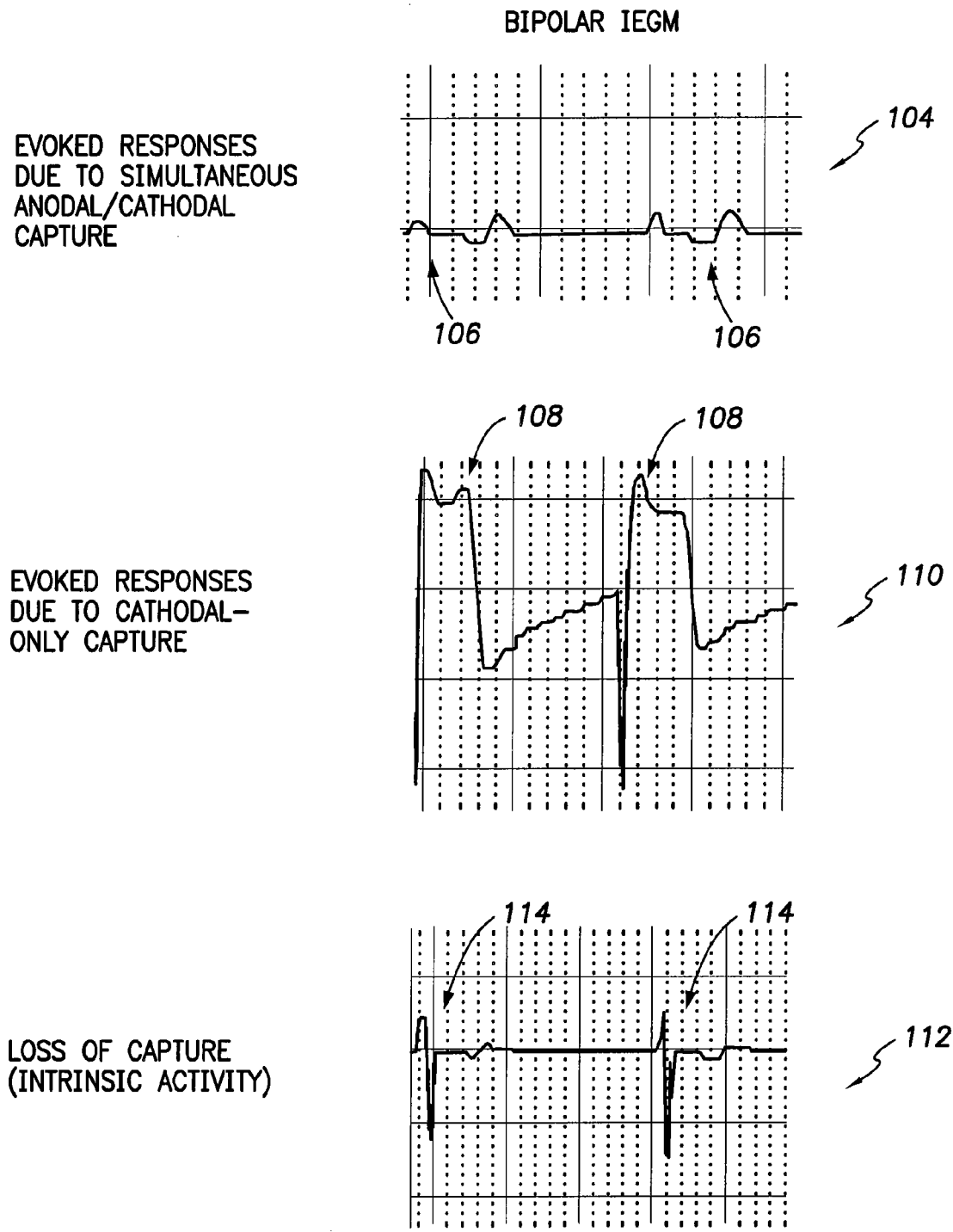
FIG. 3 is a graph illustrating the three morphologies observed within bipolar IEGMs and exploited by the technique of FIG. 2 to assess and control concurrent anodal/cathodal capture.

FIGS. 2 and 3 broadly summarize techniques exploited by the pacer/CRT of FIG. 1 (or other suitably-equipped systems) for assessing and controlling anodal/cathodal capture. Beginning at step 100 of FIG. 2, the pacer/CRT delivers bipolar stimulus (such as pacing stimulus) using a pair of electrodes of a bipolar pacing/sensing lead while sensing bipolar IEGM signals using the same pair of electrodes and while adjusting the magnitude of the bipolar stimulus, such as by incrementally increasing the magnitude. For example, the stimulus may be delivered using the LV D1 and LV M2 electrodes of a quad-pole LV lead in a bipolar pacing configuration. At step 102, the pacer/CRT then analyzes the sensed bipolar IEGM signals to detect an indication of ERs indicative of concurrent anodal/cathodal capture (the anodal capture arising within myocardial tissues associated with an anode of the electrode pair and the cathodal capture arising within myocardial tissues associated with a cathode of the electrode pair.)

FIG. 3 illustrates ERs associated with concurrent anodal/cathodal capture within a bipolar IEGM by way of exemplary graph 104, which shows the relatively low magnitude bipolar ERs 106 indicative of isoelectric ERs. In contrast, the much higher magnitude ERs 108 arising during cathodal-only capture are illustrated by way of graph 110. It is believed, within at least some patients, the lower ERs associated with concurrent anodal/cathodal capture are due to isoelectric activation, which differs from the type of myocardial activation achieved with cathodal-only capture. Note that the magnitude of an ER can be quantified using a variety of techniques such as by exploiting paced depolarization integral (PDI) or the like, as discussed in greater detail below. When evaluating or comparing the sizes or magnitude of ERs, the device can exploit any suitable quantified value such as PDI. Note also that the ERs associated with concurrent anodal/cathodal capture are typically isoelectric within healthy patients but might not be isoelectric within patients subject to cardiological disease states (and hence subject to device implantation.) Still further, the ERs associated with concurrent anodal/cathodal capture may have a different morphology or shape on the bipolar IEGM channel compared to cathodal-only capture and in many cases may be considered substantially isoelectric.

FIG. 3 also shows an exemplary bipolar IEGM 112 arising without pulse capture, which exhibits intrinsic events (QRS complexes and T-waves) 114. Hence, the figure illustrates the three distinct morphologies (or regimes) of activation observed within bipolar IEGMs: (1) low magnitude ERs associated with concurrent anodal/cathodal capture; (2) high magnitude ERs associated with cathodal-only capture; and (3) no ERs associated with pulses at either the anode or cathode (e.g. intrinsic activation following non-capture.) Note that, in this case there are intrinsic depolarizations following a non-capturing pace pulse. This is not always the case. Indeed, pacemaker dependent patients typically do not have intrinsic activity following non-captured pulses and, if there is an intrinsic depolarization, the depolarization will typically be much slower than in non-pacemaker dependent patients. Returning to FIG. 2, at step 116, the pacer/CRT determines a threshold ($CAP_{ANODE/CATHODE}$) sufficient to achieve both anodal and cathodal capture within the myocardial tissues adjacent the anode and cathode electrodes of the bipolar pair. At step 118, the pacer/CRT sets the pulse magnitude for subsequent stimulus relative to $CAP_{ANODE/CATHODE}$ to selectively enable or disable anodal and cathodal capture for particular pairs of electrodes. For example, to enable anodal/cathodal capture between the LV D1 and LV M2 electrodes, the device sets the pulse magnitude for pulses delivered along that vector above the detected anodal/cathodal capture threshold ($CAP_{ANODE/CATHODE}$) for that particular pair of electrodes. To disable anodal/cathodal capture, the device sets the pulse magnitude below $CAP_{ANODE/CATHODE}$. For example, where cross-chamber stimulus is applied via the LV D1 electrode and the RV ring electrode, it may be advantageous to disable anodal capture at the RV ring and hence the pulse magnitude may be set below the $CAP_{ANODE/CATHODE}$ threshold for that particular pair of electrodes. As noted above, while many factors influence whether a given stimulation pulse effectuates capture, a principal factor is the energy of the stimulation pulse. The energy of the stimulation pulse, in turn, is determined by the amplitude and width (or duration) of the stimulation pulse generated by the pacemaker and the electrical resistance of the pacemaker system/tissue interface circuit. Accordingly, either or both of the amplitude and pulse width of the stimulation pulse may be adjusted to set the magnitude of the stimulation pulse to selectively enable or disable anodal/cathodal capture. Techniques for use by pacer/CRTs for selectively adjusting amplitudes and pulse widths of stimulus pulses are well known and will not be described in detail herein. Note that, in circumstances where cathodal-only stimulation is employed, any safety margin applied to cathodal-only pulses to ensure capture should be set low enough such that the pulses do not inadvertently trigger anodal/cathodal stimulation.

The general techniques of FIGS. 2 and 3 will now be described in more detail with reference to various illustrative examples.

Bipolar Techniques for Concurrent Anodal/Cathodal Capture

Figure 4:
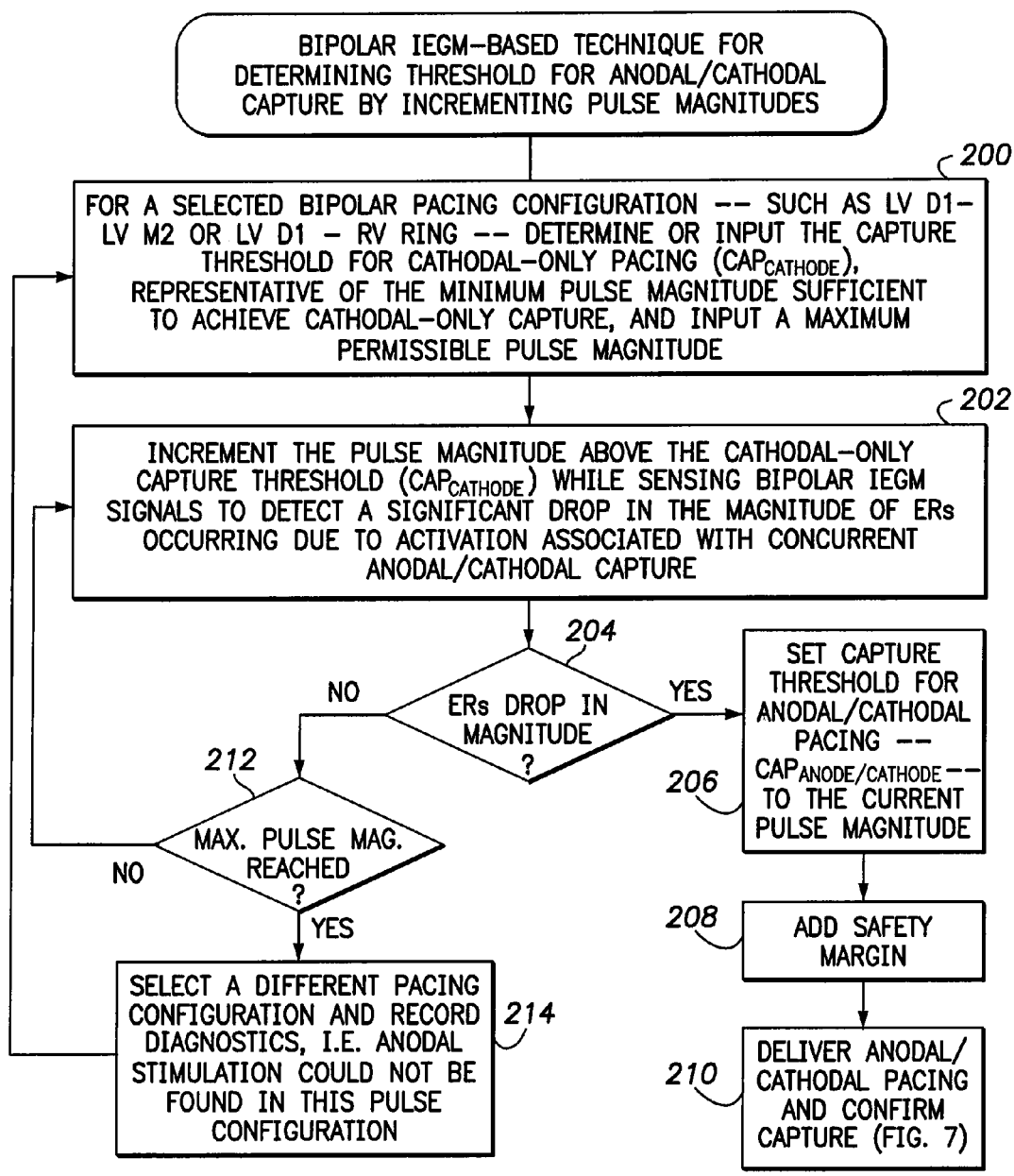
FIG. 4 illustrates an exemplary bipolar technique for determining the concurrent anodal/cathodal capture threshold in accordance with the general technique of FIG. 2 wherein bipolar IEGMs are exploited and pulse magnitudes are incremented above a capture-only threshold.
Figure 5:
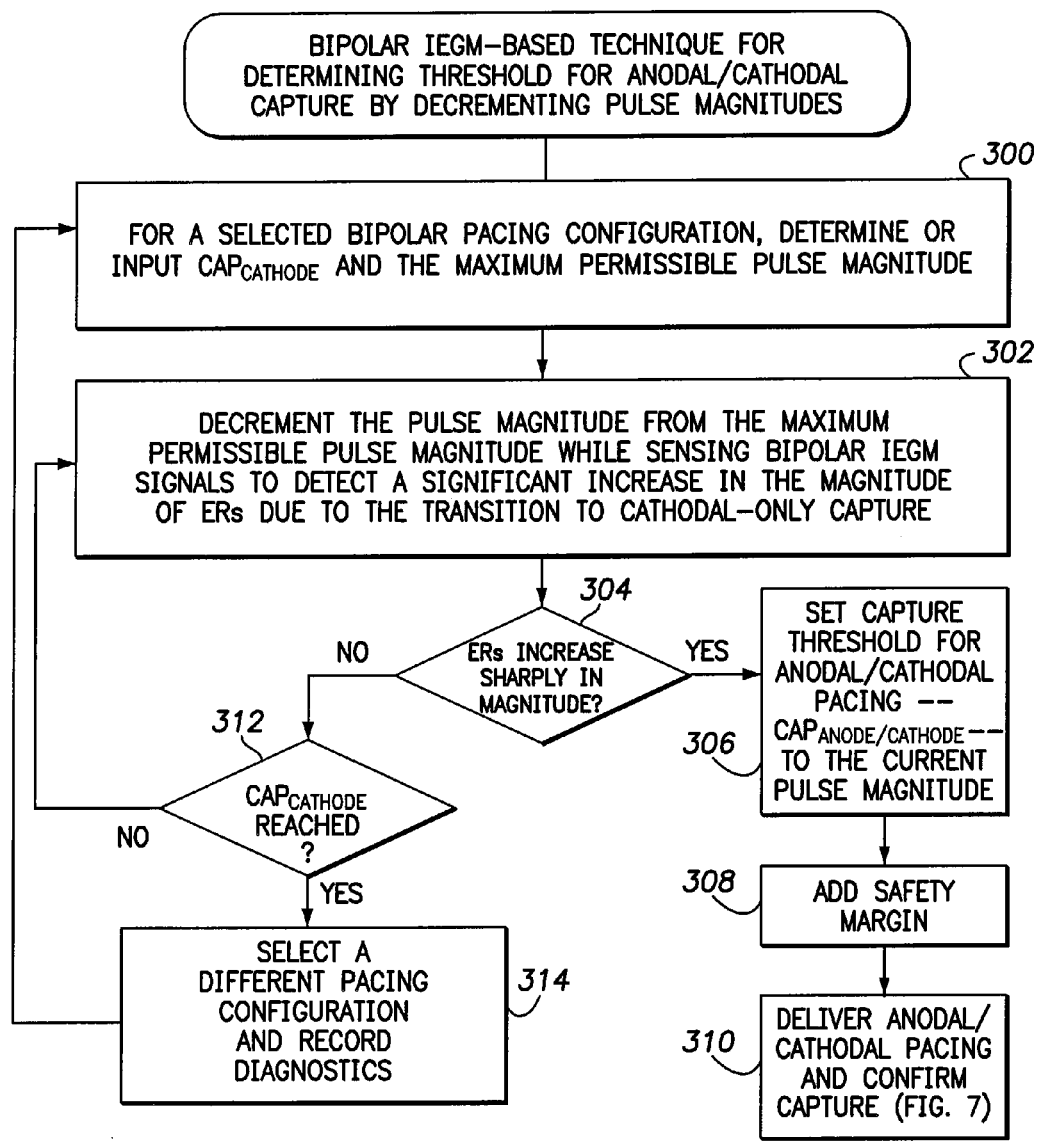
FIG. 5 illustrates another exemplary bipolar technique similar to the technique of FIG. 4 but where pulse magnitudes are decremented from a maximum pulse magnitude.
Figure 6:
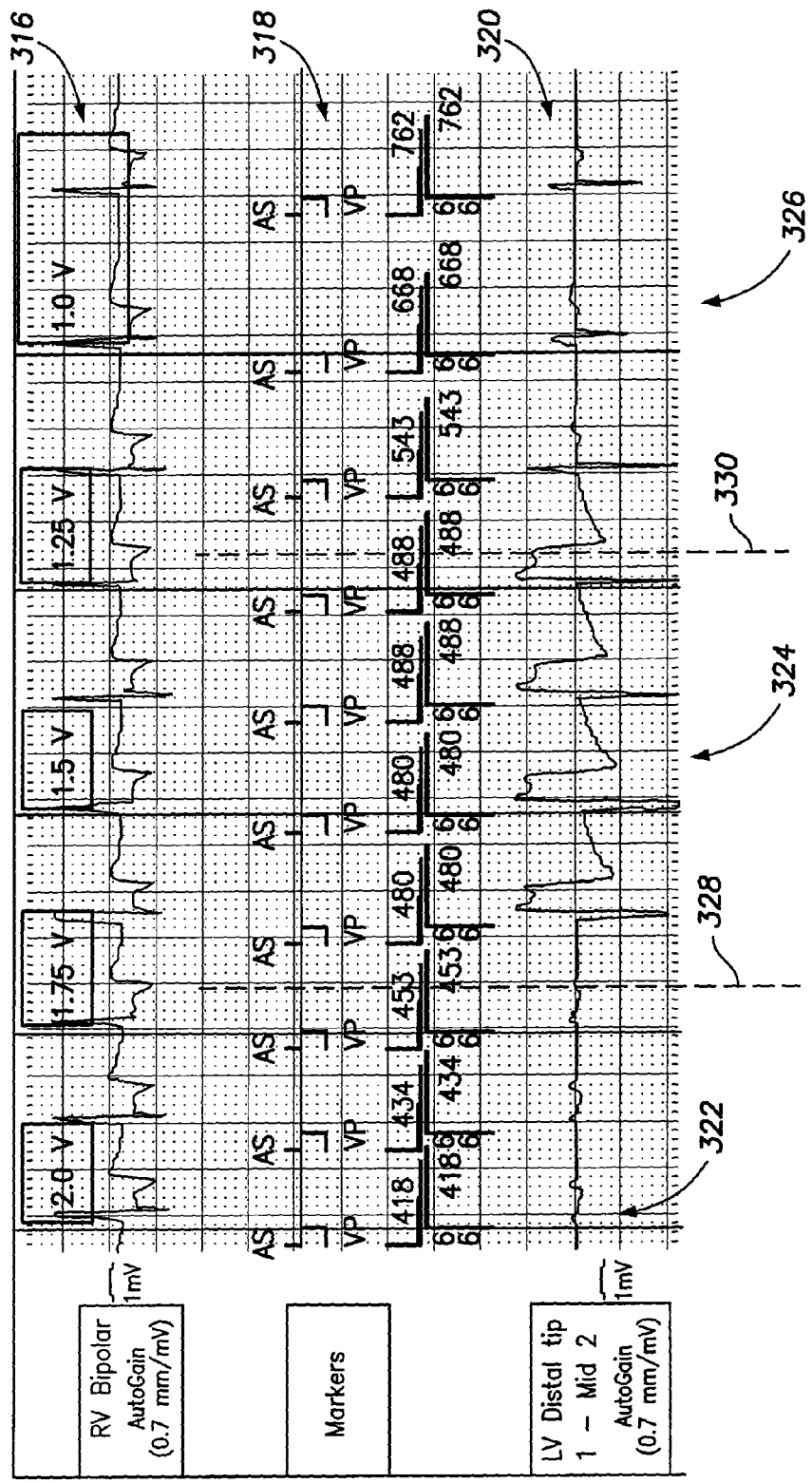
FIG. 6 presents IEGM traces illustrating exemplary bipolar IEGM signals exploited with the technique of FIG. 5 to set the concurrent anodal/cathodal capture threshold and subsequently verify capture.
Figure 7:
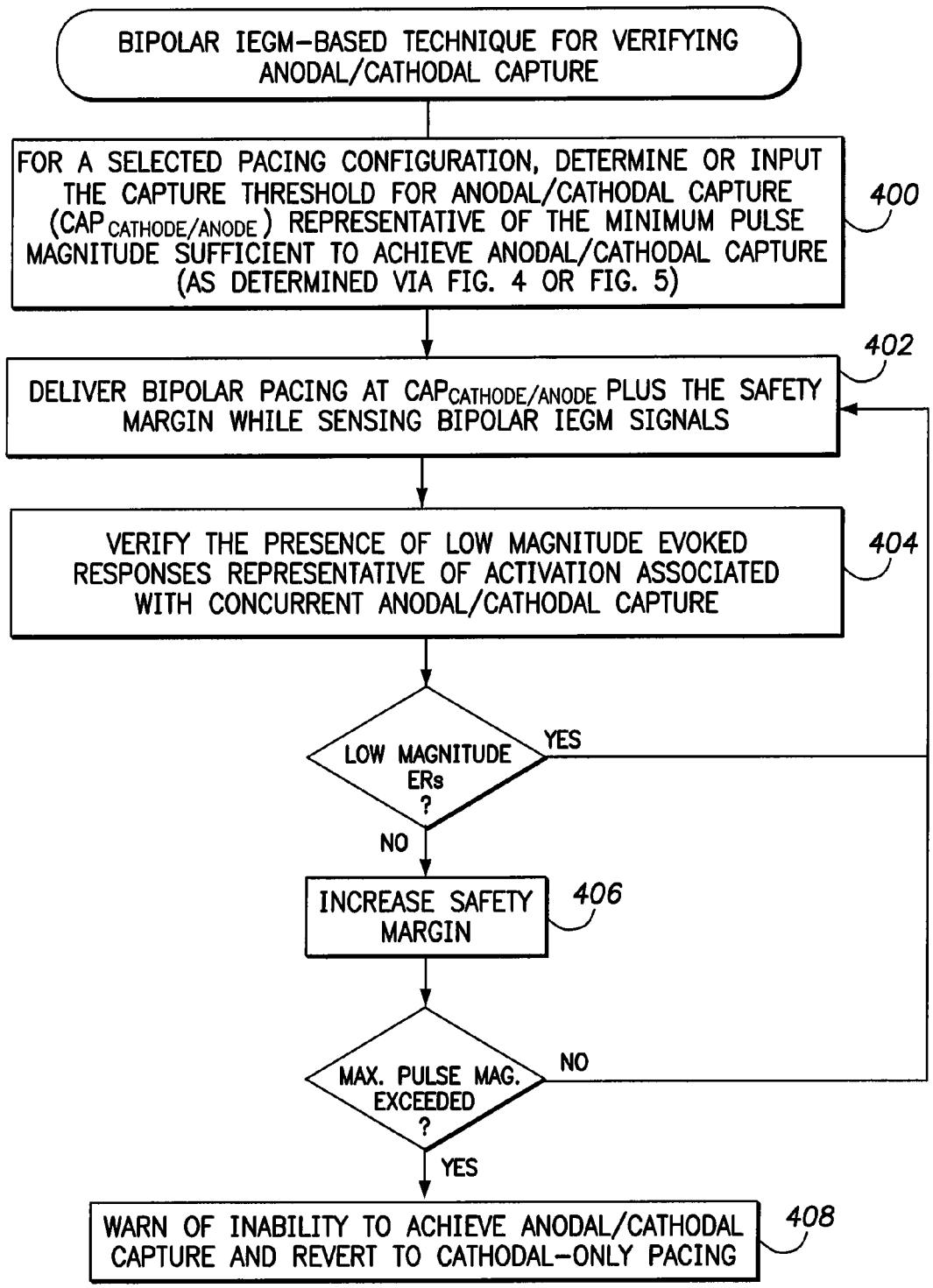
FIG. 7 illustrates an exemplary bipolar technique for verifying concurrent anodal/cathodal capture for use with techniques of FIGS. 4-6.
Figure 8:
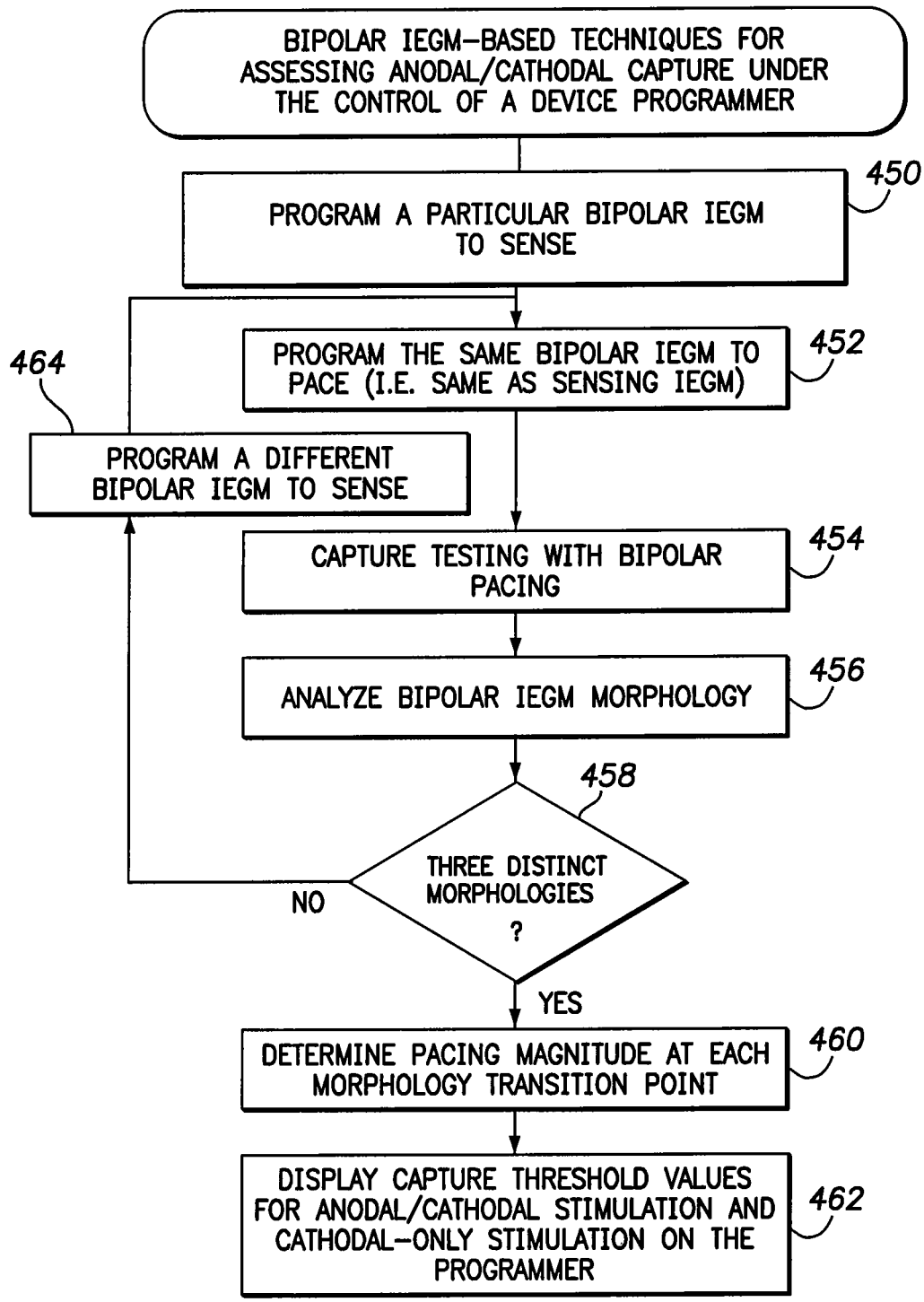
FIG. 8 illustrates a programmer-based method for performing or controlling the bipolar techniques of FIGS. 4-7.

FIGS. 4-8 illustrate techniques where concurrent anodal/cathodal capture are assessed and controlled based on bipolar IEGM signals. More specifically, FIG. 4 shows a technique for setting pulse magnitudes to achieve concurrent anodal/cathodal capture wherein test pulse magnitudes are incremented from a cathodal-only capture threshold to detect the sharp drop in ER magnitude due to concurrent anodal/cathodal capture. FIG. 5 shows an alternative technique for setting the pulse magnitude wherein test pulse magnitudes are decremented from a maximum pulse magnitude to detect the sharp increase in ER magnitude caused by switching to cathodal-only capture. FIG. 6 illustrates exemplary RV and LV bipolar IEGMs and event markers used in the process of FIG. 5. FIG. 7 shows techniques for verifying capture of pulses intended to achieve concurrent anodal/cathodal capture. FIG. 8 provides an overview of these techniques as controlled by a device programmer. (Techniques that correspond to those of FIGS. 4-8 but additionally exploit unipolar IEGM signals are described below in connection with FIGS. 9-13.)

Beginning at step 200 of FIG. 4, for a selected bipolar pacing configuration (such as LV D1-LV M2 or LV D1-RV RING), the pacer/CRT determines or inputs the capture threshold for cathodal-only pacing ($CAP_{CATHODE}$), representative of the minimum pulse magnitude sufficient to achieve cathodal-only capture when bipolar pulses are applied. This capture threshold, which is lower than the capture threshold for anodal/cathodal capture, may be determined using otherwise conventional automatic stimulation threshold search systems such as the AUTOCAPTURE™ capture detection system of St. Jude Medical, which applies a sequence of stimulation pulses with differing pulse amplitudes so as to determine the lowest amplitude sufficient to effectuate capture (i.e. cathodal-only capture). An example of the AUTOCAPTURE™ system is described within U.S. Pat. No. 5,417,718 to Kleks et al., entitled "System for Maintaining Capture in an Implantable Pulse Generator." See, also, U.S. Pat. No. 7,899,536 to Hellman et al., entitled "Morphology Discrimination for Capture Assessment" and U.S. Pat. No. 7,706,865 to Snell, entitled "Apparatus and Method for Cardiac Rhythm Detection" as well as U.S. Published Patent Application 2010/0042176 also of Snell, entitled "Temporal-Based Cardiac Capture Threshold Detection."

At step 200, the pacer/CRT also inputs a maximum permissible pulse magnitude, which may be, e.g., 2.0 Volts.

At step 202, the pacer/CRT then increments the pulse magnitude above the cathodal-only capture threshold ($CAP_{CATHODE}$) while sensing bipolar IEGM signals to detect a significant drop in the magnitude of evoked responses occurring due to the isoelectric activation associated with concurrent anodal/cathodal capture. If, at decision step 204, the ERs are found to drop significantly in magnitude then, at step 206, the capture threshold for concurrent anodal/cathodal pacing ($CAP_{ANODE/CATHODE}$) is set to the current pulse magnitude. To determine whether a drop in ER magnitude is deemed significant, programmed thresholds may be employed, set subject to clinician approval. To ensure that subsequent pulses are set high enough above the $CAP_{ANODE/CATHODE}$ to reliably achieve concurrent anodal/cathodal capture, a safety margin might be applied at step 208, which is a preprogrammed value added to the $CAP_{ANODE/CATHODE}$ pulse magnitude, also set subject to clinician approval. (Note that, if a safety margin is applied, the safety margin would not need to be as high as the safety margin for the difference between capture and no capture at all.) At step 210, the pacer/CRT then commences delivery of concurrent anodal/cathodal pacing while confirming capture (using techniques of FIG. 7.)

Returning to step 204, if the ERs are not found to have dropped significantly in magnitude then, at step 212, the pacer/CRT determines whether the current pulse magnitude can be further increased (or whether the maximum permissible pulse magnitude has already been achieved.) If the pulse magnitude can be increased further, then processing returns to step 202 where the pulse magnitude is incremented yet again. The amount by which the pulse magnitude is incremented during each iteration of the procedure may be a preprogrammed value, set subject to clinician approval. If the process is repeated until the pulse magnitude can no longer be increased because it has already reached the maximum permissible magnitude and the ERs have not dropped in magnitude in accordance with concurrent anodal/cathodal capture then, at step 214, the pacer/CRT switches to a different pacing configuration (in accordance with pre-programmed instructions set subject to clinician approval) in an attempt to find an alternate configuration sufficient to achieve anodal/cathodal capture. (That is, in this case, anodal stimulation could not be found in this pulse configuration. For example, whereas the LV D1/P4 pair might not achieve concurrent anodal/cathodal capture within a particular patient, the LV D1/M3 pair might achieve such capture and so the search procedure would be repeated for the newly selected pair. In the event that all permissible bipolar pulse delivery pairs are tested without finding one that achieves concurrent anodal/cathodal capture, then suitable diagnostics and messages are generated to alert and inform the clinician.

Turning now to FIG. 5, an alternative technique wherein the pulse magnitude is decremented will now be briefly described. Many of the steps are the same or similar to those of FIG. 4. At step 300, for a selected bipolar pacing configuration, the pacer/CRT determines or inputs $CAP_{CATHODE}$ and the maximum permissible pulse magnitude. At step 302, the pacer/CRT then decrements the pulse magnitude from the maximum permissible pulse magnitude while sensing bipolar IEGM signals to detect a significant and sharp increase in ER magnitude occurring due to the transition to cathodal-only capture. If, at step 304, the ERs are found to increase significantly then, at step 306, $CAP_{ANODE/CATHODE}$ is set to the current pulse magnitude. To determine whether an increase in ER magnitude is deemed significant, programmed thresholds may again be used, set subject to clinician approval. A safety margin may be applied at step 308 before delivery of concurrent anodal/cathodal pacing commences at step 310.

Returning briefly to step 304, if the ERs are not found to have increased significantly then, at step 312, the pacer/CRT determines whether the current pulse magnitude can be decreased further while still remaining above $CAP_{CATHODE}$ and, if so, processing returns to step 302 where the pulse magnitude is decremented again. The amount by which the pulse magnitude is decremented during each iteration may be a pre-programmed value, set subject to clinician approval. If the process is repeated until the pulse magnitude can no longer be decreased because it has already been lowered to $CAP_{CATHODE}$ and the ERs have not increased significantly in magnitude then, at step 314, the pacer/CRT may switch to a different pacing configuration (in accordance with pre-programmed instructions subject to clinician approval). In the event that all permissible bipolar pulse delivery pairs are tested without determining $CAP_{ANODE/CATHODE}$, then suitable diagnostics and messages are generated to alert and inform the clinician.

FIG. 6 illustrates various exemplary IEGMs and event marker recordings obtaining via the procedure of FIG. 5 wherein pulse magnitudes are decremented from a maximum permissible value. More specifically, a first IEGM trace 316 illustrates an RV bipolar IEGM trace showing paced QRS complexes (or evoked responses) and T-waves observed while pacing pulses of decrementing magnitudes are delivered to the LV via D1/M2. In this example, pulse magnitudes begin at 2.0V and are decremented until capture is completely lost at 1.0 V. A set of event makers 318 illustrate the timing of pacing events as well as various otherwise conventional delay intervals. A second IEGM trace 320 illustrates the LV bipolar IEGM trace sensed via the D1/M2 pair, showing relatively low magnitude ERs associated with concurrent anodal/cathodal capture 322, relatively high magnitude ERs associated with cathodal-only capture 324 and intrinsic QRS complexes and T-waves 326 associated with complete loss of capture.

In this example, as the pulse magnitude is decremented, the magnitudes of the bipolar ERs increases sharply below a pulse magnitude of about 1.6 V indicating that, for this patient, $CAP_{ANODE/CATHODE}$ is found at about that level. Note, however, that the Capture Threshold is the minimum amplitude/width that results in consistent capture. Accordingly, in this example, a value of 1.5 V may be used for the cathodal capture threshold whereas a value of 2.0 V may be used as the anodal/cathodal capture threshold ($CAP_{ANODE/CATHODE}$.) Note also that the VP value shown in the figure (that is aligned with the voltage markers) is set at the prior amplitude, which is why one pulse captures and another does not capture at 1.75 V and 1.25 V. The $CAP_{ANODE/CATHODE}$ threshold is shown by way of vertical line 328. Still further, as the pulse magnitude decreases even more, capture is completely lost at about 1.2V indicating that, for this patient, $CAP_{CATHODE}$ is found at about that level. The $CAP_{CATHODE}$ threshold is shown by way of vertical line 330.

Thus, FIGS. 4-6 illustrate various bipolar techniques for determining $CAP_{ANODE/CATHODE}$ and selectively setting the pulse magnitudes for concurrent anodal/cathodal capture.

FIG. 7 illustrates techniques for verifying capture of the pulses to ensure that anodal/cathodal capture is indeed being achieved. Beginning at step 400, for a selected pacing configuration, the pacer/CRT determines or inputs the capture threshold for anodal/cathodal capture ($CAP_{ANODE/CATHODE}$), which is representative of the minimum pulse magnitude sufficient to achieve concurrent anodal/cathodal capture as determined using the techniques of FIG. 4 or 5. At step 402, the pacer/CRT then delivers bipolar pacing at $CAP_{ANODE/CATHODE}$ plus the aforementioned safety margin while sensing bipolar IEGM signals and, at step 404, verifies the presence of low magnitude ERs representative of isoelectric activation associated with concurrent anodal/cathodal capture (such as the low magnitude pulses 322 of FIG. 6.) This may be achieved by comparing ER magnitude with suitable magnitude ranges or thresholds set while $CAP_{ANODE/CATHODE}$ is being determined. For example, if the magnitude of the ERs falls below a threshold indicative of anodal/cathodal ERs, then the ER is deemed to be the result of concurrent anodal/cathodal capture. If the magnitude exceeds the threshold, then the ER is deemed to be the result cathodal-only capture, i.e. concurrent anodal/cathodal capture has been lost. (If no ERs are detected, then complete LOC is detected.)

Assuming that anodal/cathodal capture has been verified via low magnitude ERs, then processing returns to step 402 for further pacing. If not, then the safety margin can be increased at step 406 and another pulse delivered at step 402. If the safety margin is increased to the point where the maximum permissible pulse magnitude is exceeded, then at step 408, generates warnings to alert the clinician of the inability to achieve concurrent anodal/cathodal capture within the patient. The pacer/CRT then reverts to cathodal-only pacing or performs other pre-programmed actions.

FIG. 8 illustrates operations performed by a device programmer for performing or controlling the procedures of FIGS. 4-7. As many of these procedures have already been described in FIGS. 4-7, the steps of FIG. 8 will only briefly be summarized. Beginning at step 450, the programmer sends signals to the implanted pacer/CRT to program a particular bipolar sensing IEGM, such as the LV D1/M2 vector. At step 452, the programmer sends signals to the pacer/CRT to program the same bipolar IEGM to also pace so that the bipolar IEGM will be derived for the same bipolar pair of electrodes used to deliver bipolar stimulation. At step 454, the programmer performs or controls capture testing using the selected bipolar electrodes by, for example, increasing pulse magnitude from zero up to a pulse maximum while recording the resulting IEGM morphologies. At step 456, the programmer then analyzes the resulting bipolar IEGM morphologies to detect the three distinct morphologies discussed above.

Assuming all three morphologies are observed (at different ranges of pulse magnitudes) within the bipolar IEGM at step 458, then the programmer determines the pacing magnitudes at each morphology transition point at step 460, i.e. the transition from no ERs to high-magnitude cathodal ERs, and then the transition from high-magnitude cathode ERs to lower magnitude isoelectric anodal/cathodal ERs within the bipolar IEGM. At 462, the programmer displays capture threshold values for anodal/cathodal stimulation and cathodal-only stimulation on the programmer for clinician review. If, at step 458, all three morphologies were not observed (likely indicating that concurrent anodal/cathodal was not achieved despite even high pulse magnitudes), the programmer sends signals at step 464 to the pacer/CRT to reprogram the bipolar IEGM to sense using a different pair of electrodes so that the procedure may be repeated with a different bipolar pair to detect both the anodal/cathodal capture threshold and the cathodal-only capture threshold. In the event that none of the available pairs of electrodes suffice to determine both the anodal/cathodal capture threshold and the cathodal-only capture threshold, suitable message may be displayed for the clinician.

Bipolar/Unipolar Techniques for Concurrent Anodal/Cathodal Capture

FIGS. 9-13 illustrate alternative techniques where concurrent anodal/cathodal capture are assessed and controlled based on a comparison of bipolar and unipolar IEGM signals. Some of the aspects of these alternative techniques are similar to those of FIGS. 4-8 and hence will not be described in detail again. Beginning at step 500 or FIG. 9, for a selected bipolar pacing configuration, the pacer/CRT determines or inputs $CAP_{CATHODE}$ and also inputs the maximum permissible pulse magnitude. At step 502, the pacer/CRT then increments the pulse magnitude above $CAP_{CATHODE}$ while sensing both bipolar and unipolar IEGM signals to detect a significant drop in the magnitude of ERs within the bipolar IEGM but not the unipolar IEGM (and where the unipolar cathode electrode is the same as the bipolar cathode electrode.) Note that, insofar as quantifying the evoked response, the anodal/cathodal isoelectric morphology will have a low PDI or DMAX value, which can make it difficult in some cases for the device to distinguish the response from total non-capture. However, in combination with the unipolar IEGM, which confirms that there is still at least cathodal capture (and will typically have a high PDI or DMAX value), the device can thereby detect that the bipolar evoked response is different from non-capture. The bipolar IEGM may be derived from, e.g., the D1-M2 pair, whereas the unipolar IEGM may be derived D1—can using otherwise conventional techniques. As noted above, the bipolar IEGM exhibits three distinct morphologies: (1) low magnitude ERs associated with concurrent anodal/cathodal capture; (2) high magnitude ERs associated with cathodal-only capture; and (3) no ERs associated with lack of capture at either the anode or cathode. In contrast, the unipolar IEGM exhibits only two distinct morphologies: (1) high magnitude ERs associated with capture either at the cathode or at both the anode and cathode; and (2) no ERs associated with lack of capture at either the anode or cathode. Accordingly, a comparison of the two IEGM signals at various pulse magnitudes can be used to detect $CAP_{ANODE/CATHODE}$ by detecting the drop in ER magnitude that occurs within the bipolar IEGM but not within the unipolar IEGM when concurrent anodal/cathodal capture is achieved.

If, at decision step 504, the magnitudes of the bipolar IEGM ERs are found to be small while capture can still be confirmed via unipolar ERs then, at step 506, $CAP_{ANODE/CATHODE}$ is set to the current pulse magnitude. To determine whether the magnitude of the bipolar ER is deemed small or low, programmed thresholds may be used, set subject to clinician approval. At step 508, a safety margin might be added and, at step 510, the pacer/CRT commences delivery of concurrent anodal/cathodal pacing while confirming capture (using techniques of FIG. 12.) Conversely, at step 504, if the magnitude of the bipolar IEGM ERs are sufficiently large (or capture cannot be confirmed via unipolar IEGM ERs) then, at step 512, the pacer/CRT determines whether the current pulse magnitude can be decreased further while still remaining above $CAP_{CATHODE}$ and, if so, processing returns to step 502 where the pulse magnitude is decremented again. If the process is repeated until the pulse magnitude can no longer be decreased because it has already reached $CAP_{CATHODE}$ yet concurrent anodal/cathodal capture has not been detected, then, at step 514, the pacer/CRT may switch to a different pacing configuration (in accordance with pre-programmed instructions subject to clinician approval). In the event that all permissible bipolar pulse delivery pairs are tested without finding one that achieves concurrent anodal/cathodal capture, then suitable diagnostics and messages are generated to alert and inform the clinician.

Figure 10:
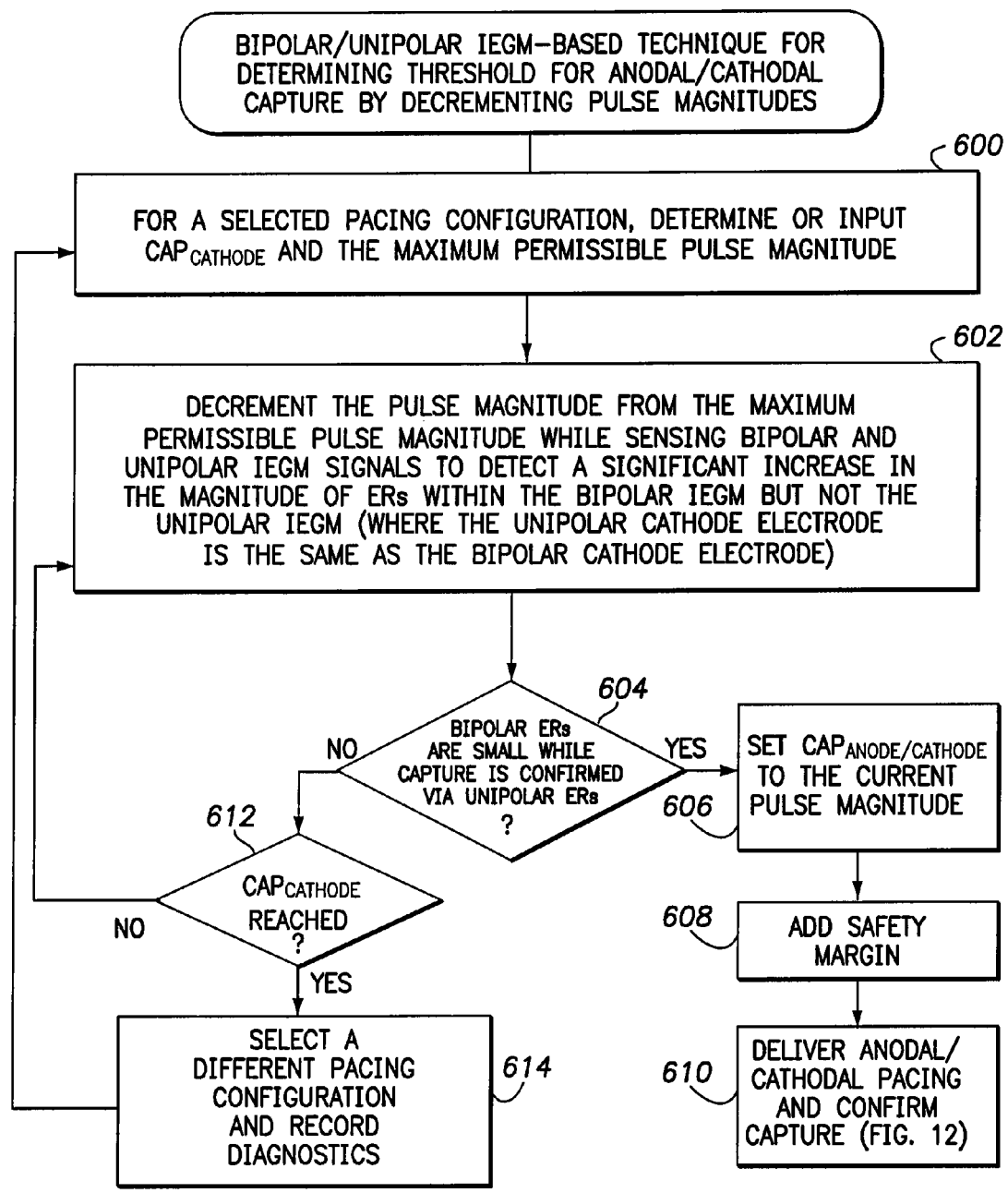
FIG. 10 illustrates another exemplary bipolar/unipolar technique similar to the technique of FIG. 9 but where pulse magnitudes are decremented from a maximum pulse magnitude.

Turning now to FIG. 10, an alternative bipolar/unipolar technique wherein the pulse magnitude is decremented will now be briefly described. At step 600, for a selected bipolar pacing configuration, the pacer/CRT determines or inputs $CAP_{CATHODE}$ and the maximum permissible pulse magnitude. At step 602, the pacer/CRT then decrements the pulse magnitude from the maximum permissible pulse magnitude while sensing bipolar IEGM signals and unipolar IEGM signals to detect a significant increase in the magnitude of ERs within the bipolar IEGM but not within the unipolar IEGM (and where the unipolar cathode electrode is the same as the bipolar cathode electrode.) If, at step 604, the magnitudes of the bipolar IEGM ERs are found to be small while capture can still be confirmed via unipolar ERs, then, at step 606, $CAP_{ANODE/CATHODE}$ is set to the current pulse magnitude. A safety margin may be applied at step 608 before delivery of concurrent anodal/cathodal pacing commences at step 610.

Returning briefly to step 604, if the ERs within the bipolar IEGM are sufficiently large (or capture cannot be confirmed via unipolar IEGM ERs), then, at step 612, the pacer/CRT determines whether the current pulse magnitude can be decreased further while still remaining above $CAP_{CATHODE}$ and, if so, processing returns to step 602 where the pulse magnitude is decremented again. If the process is repeated until the pulse magnitude can no longer be decreased because it has already reached $CAP_{CATHODE}$ then, at step 614, the pacer/CRT may switch to a different pacing configuration (in accordance with pre-programmed instructions subject to clinician approval) in an attempt to find an alternate configuration sufficient to achieve concurrent anodal/cathodal capture. In the event that all permissible bipolar pulse delivery pairs are tested without finding one that achieves concurrent anodal/cathodal capture, then suitable diagnostics and messages are generated to alert and inform the clinician.

FIG. 11 illustrates bipolar and unipolar IEGMs and event marker recordings obtaining via the procedure of FIG. 10 wherein pulse magnitudes are decremented from a maximum permissible value. As with FIG. 6, a first IEGM trace 616 illustrates an RV bipolar IEGM trace showing paced QRS complexes and T-waves observed while pacing pulses of decrementing magnitudes are delivered to the LV via D1/M2. A set of event makers 618 illustrate the timing of pacing events as well as various otherwise conventional delay intervals. A second IEGM trace 620 illustrates the LV bipolar IEGM trace sensed via the D1/M2 pair, showing relatively low magnitude ERs associated with concurrent anodal/cathodal capture 622, relatively high magnitude ERs associated with cathodal-only capture 624 and intrinsic QRS complexes and T-waves 626 associated with complete loss of capture. Additionally, a third IEGM trace 628 shows a unipolar D1—can IEGM, which exhibits large ERs at all pulse magnitudes above about 1.2 V but no ERs below that level. That is, a comparison of the bipolar and unipolar IEGMs illustrates the aforementioned three bipolar ER morphologies but only two unipolar ER morphologies.

As the pulse magnitude is decremented in this example from 2.0 V, the magnitudes of the bipolar ERs drop sharply below a pulse magnitude of about 1.6V whereas the magnitudes of the unipolar ERs do not drop significantly, indicating that, for this patient, $CAP_{ANODE/CATHODE}$ is found at about that pulse level. The $CAP_{ANODE/CATHODE}$ threshold is shown by way of vertical line 630. Still further, as the pulse magnitude decreases even more, capture is completely lost at about 1.2V for both the bipolar and unipolar IEGMs indicating that, for this patient, $CAP_{CATHODE}$ is found at about that pulse level. The $CAP_{CATHODE}$ threshold is shown by way of vertical line 632.

Figure 9:
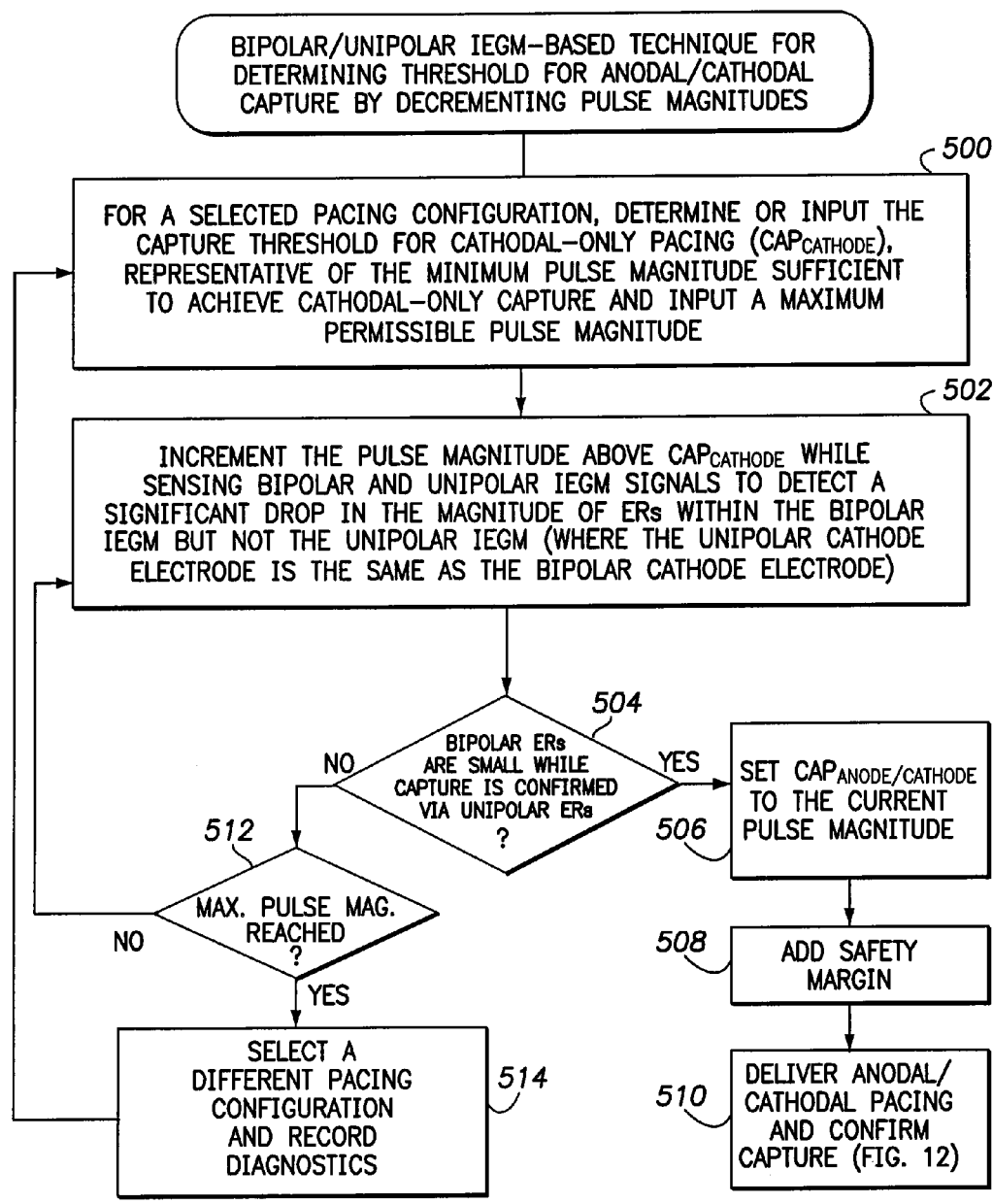
FIG. 9 illustrates an exemplary bipolar/unipolar technique for determining the concurrent anodal/cathodal capture threshold in accordance with the general technique of FIG. 2 wherein bipolar and unipolar IEGMs are exploited and pulse magnitudes are incremented above a capture-only threshold.

Thus, FIGS. 9-11 illustrate various bipolar/unipolar techniques for determining $CAP_{ANODE/CATHODE}$ and selectively setting the pulse magnitudes for concurrent anodal/cathodal capture.

Figure 12:
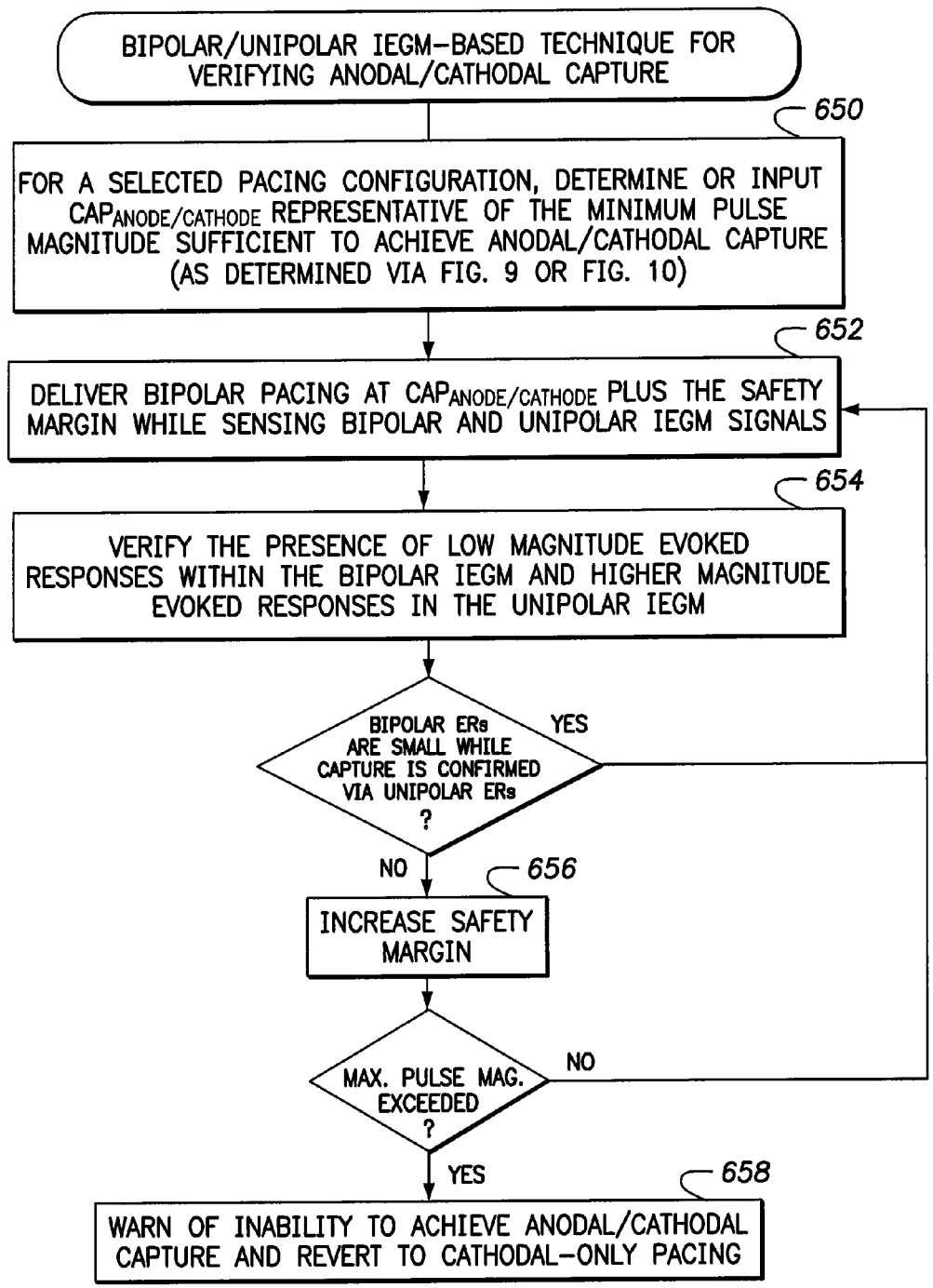
FIG. 12 illustrates an exemplary bipolar/unipolar technique for verifying concurrent anodal/cathodal capture for use with the techniques of FIGS. 9-11.

FIG. 12 illustrates techniques for verifying capture of the pulses to ensure that concurrent anodal/cathodal capture is indeed being achieved. Beginning at step 650, for a selected pacing configuration, the pacer/CRT determines or inputs $CAP_{ANODE/CATHODE}$, which is representative of the minimum pulse magnitude sufficient to achieve concurrent anodal/cathodal capture, as determined using the techniques of FIG. 9 or 10. At step 652, the pacer/CRT delivers bipolar pacing at $CAP_{ANODE/CATHODE}$ plus the aforementioned safety margin while sensing bipolar and unipolar IEGM signals and, at step 654, verifies the presence of low magnitude ERs within the bipolar IEGM and higher magnitude ERs in the unipolar IEGM (e.g. the magnitude of the bipolar IEGM ERs are small while capture can be confirmed via unipolar IEGM ERs.) This may be achieved by comparing the magnitudes of the unipolar and bipolar ERs with one another or with suitable magnitude ranges or thresholds. If the magnitude of the bipolar IEGM ERs are small while capture can be confirmed via unipolar IEGM ERs, then the ERs are deemed to be the result of concurrent anodal/cathodal capture. Conversely, then the ERs are deemed to be the result cathodal-only capture, i.e. concurrent anodal/cathodal capture has been lost. (If no ERs are detected in either the unipolar or bipolar IEGMs, then complete LOC is detected.)

Assuming that concurrent anodal/cathodal capture has been verified, processing returns to step 652 for further pacing. If not, the safety margin is increased at step 656 and another pulse delivered at step 652. If the safety margin is increased to the point where the maximum permissible pulse magnitude is exceeded, then at step 658, the device generates warnings to alert the clinician. The pacer/CRT then reverts to cathodal-only pacing or performs other pre-programmed actions.

Figure 13:
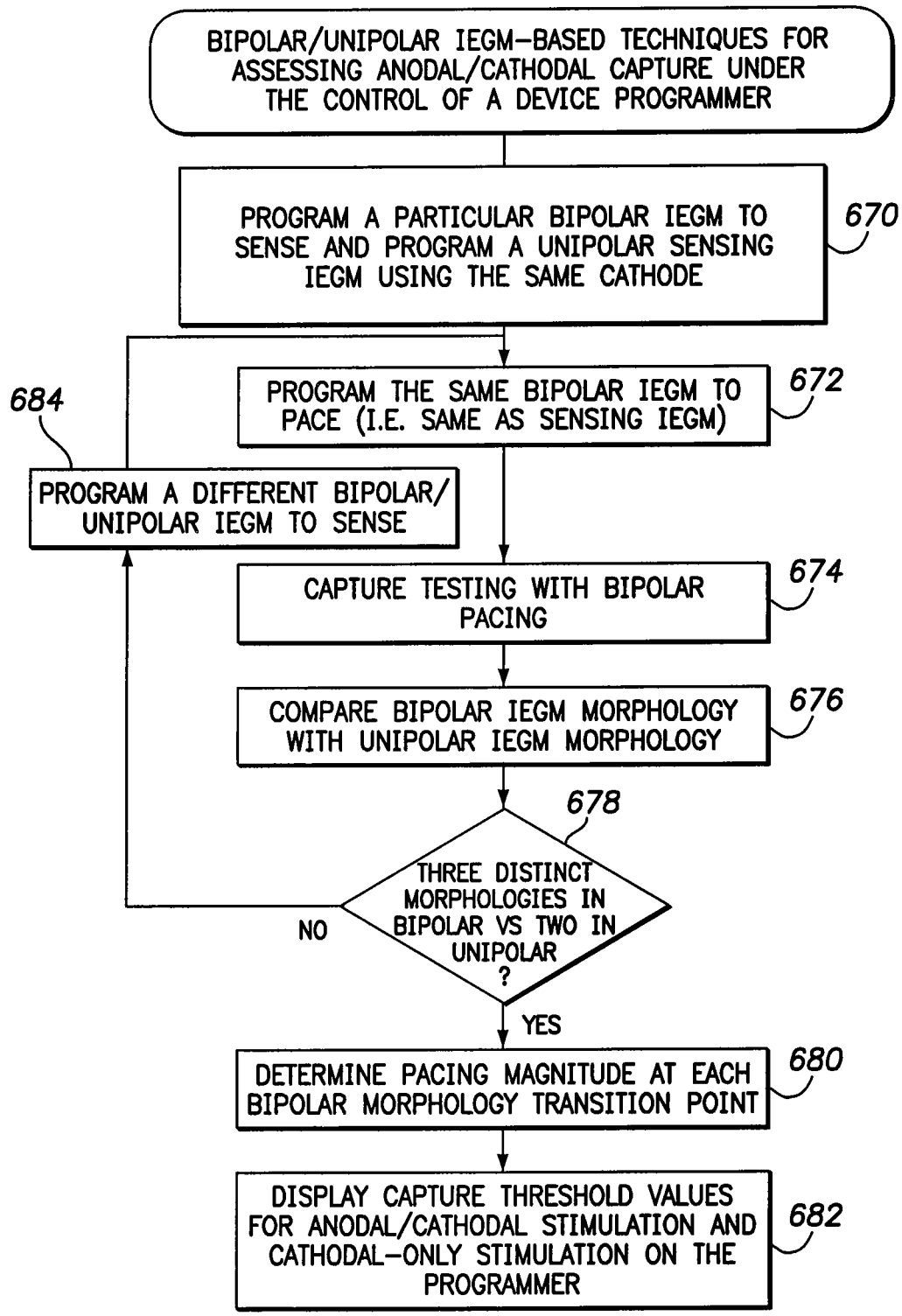
FIG. 13 illustrates a programmer-based method for performing or controlling the bipolar/unipolar techniques of FIGS. 9-12.

FIG. 13 illustrates operations performed by a device programmer for performing or controlling the procedures of FIGS. 9-12. As many of these procedures have already been described, the steps of FIG. 13 will only briefly be summarized. Beginning at step 670, the programmer sends signals to the implanted pacer/CRT to program a particular bipolar sensing IEGM, such as the LV D1/M2 vector and to also program a unipolar sensing IEGM using the same cathodal electrode. At step 672, the programmer sends signals to the pacer/CRT to program the same bipolar IEGM to also pace so that the bipolar IEGM will be derived for the same bipolar pair of electrodes used to deliver bipolar stimulation (and the unipolar IEGM will be derived from the same cathode used for bipolar pacing.) At step 674, the programmer performs or controls capture testing using the selected bipolar electrodes by, for example, increasing pulse magnitude from zero up to a pulse maximum while recording the resulting bipolar and unipolar IEGM morphologies. At step 676, the programmer then analyzes the resulting bipolar and unipolar IEGM morphologies to detect the three distinct morphologies of the bipolar IEGM as opposed to the two distinct morphologies of the unipolar IEGM.

Assuming all three morphologies are observed (at different ranges of pulse magnitudes) within the bipolar IEGM but only two morphologies are observed within the unipolar IEGM at step 678, then the programmer determines at step 680 the pacing magnitudes at each bipolar morphology transition point, i.e. the transition from no ERs to high-magnitude cathodal ERs, and then the transition from high-magnitude cathode ERs to lower magnitude isoelectric anodal/cathodal ERs, within the bipolar IEGM. At 682, the programmer displays capture threshold values for anodal/cathodal stimulation and cathodal-only stimulation on the programmer for clinician review. If, at step 678, all three morphologies were not observed (likely indicating that concurrent anodal/cathodal was not achieved despite even high pulse magnitudes), the programmer sends signals at step 684 to the pacer/CRT to reprogram the bipolar IEGM to sense using a different pair of electrodes so that the procedure may be repeated with a different bipolar pair to detect both the anodal/cathodal capture threshold and the cathodal-only capture threshold. In the event that none of the available pairs of electrodes suffice to determine both the anodal/cathodal capture threshold and the cathodal-only capture threshold, suitable messages may be displayed for the clinician.

Quad-Pole Lead-Based Techniques Exploiting Anodal/Cathodal Capture

Figure 14:
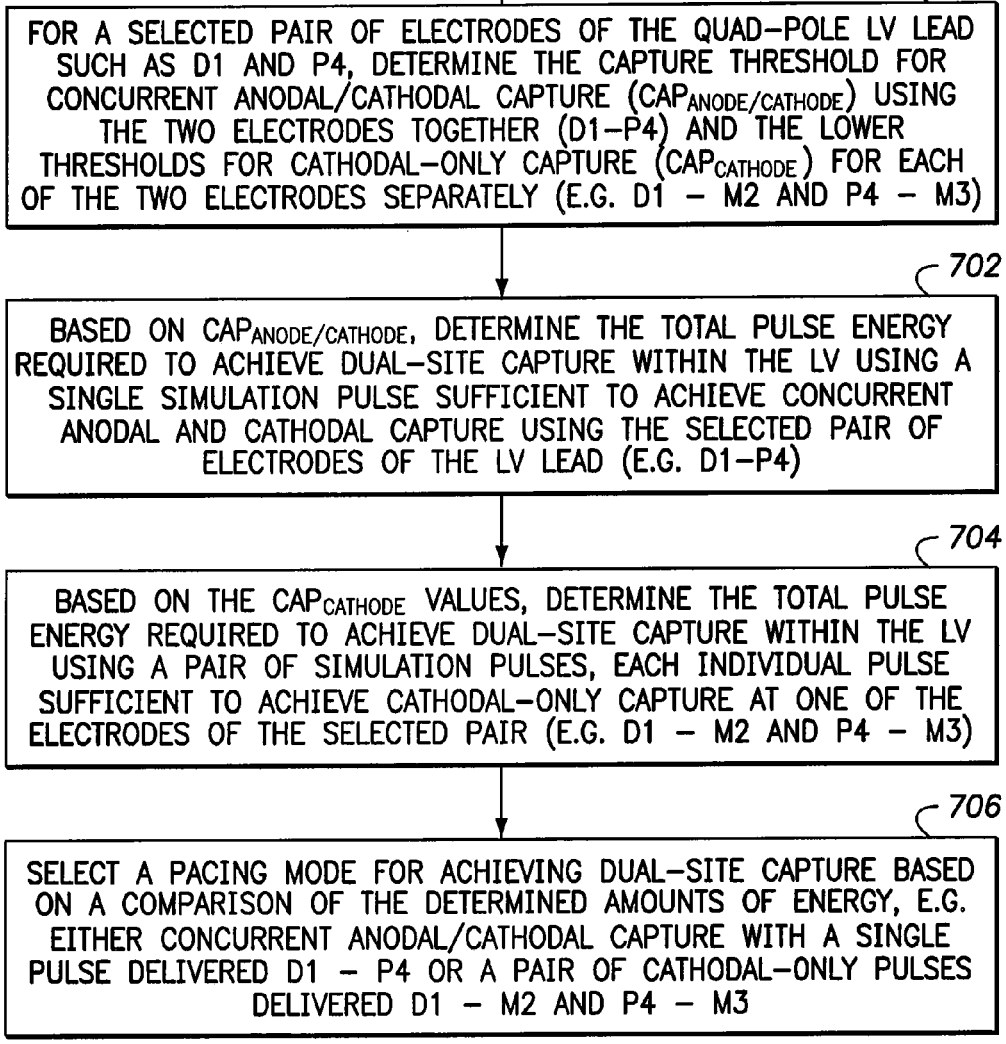
FIG. 14 illustrates an exemplary technique for use with quad-pole leads for controlling dual-site pacing that may be performed by the device of FIG. 1.
Figure 15:
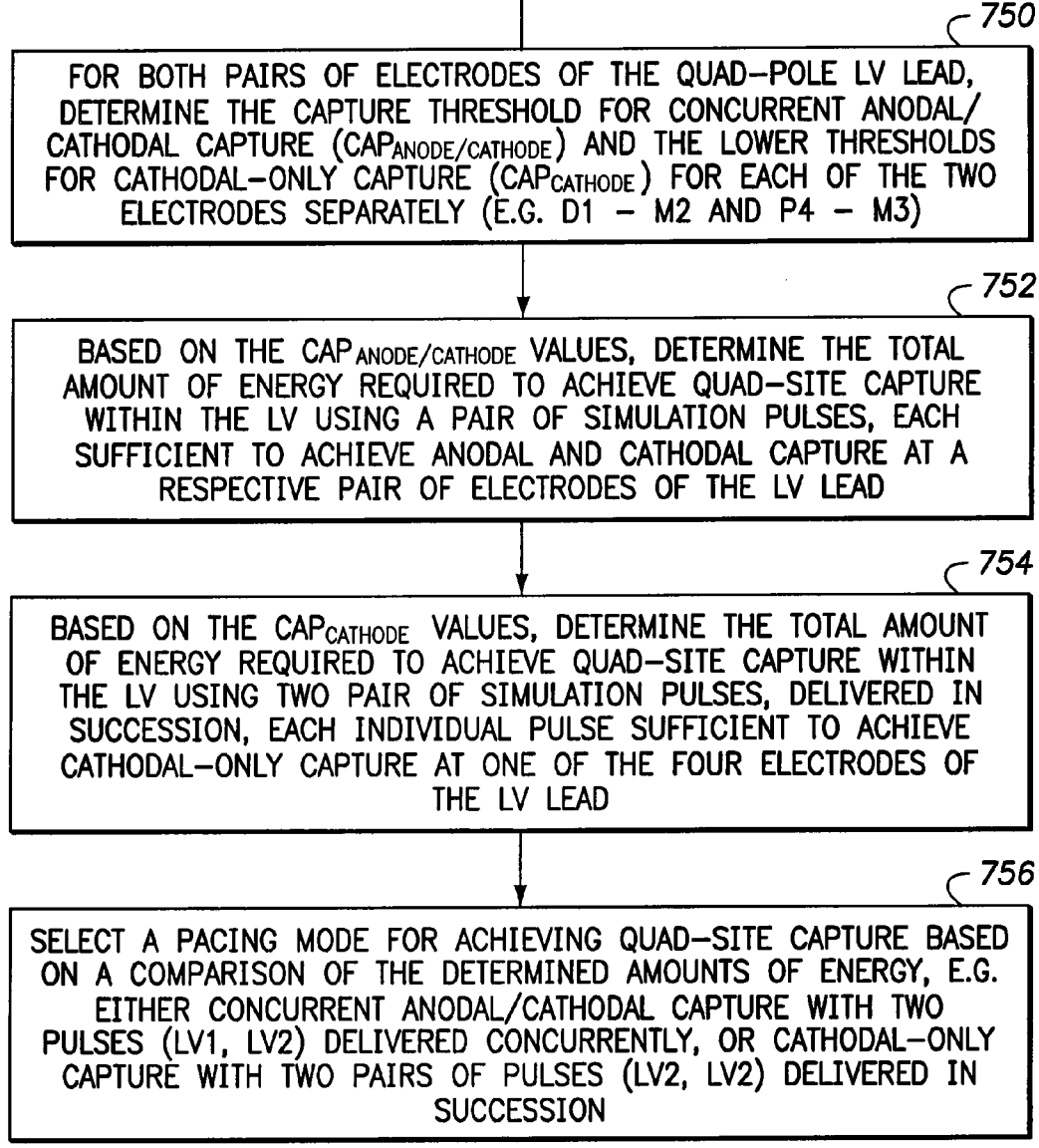
FIG. 15 illustrates an exemplary technique for use with quad-pole leads for controlling quad-site pacing that may be performed by the device of FIG. 1.

Turning now to FIGS. 14-15, techniques for use with quad-pole leads for achieving dual-site or quad-site stimulation while selectively exploiting anodal/cathodal capture will be described. These examples pertain to a device equipped to deliver two concurrent pulses to the LV: LV1 and LV2. In the example, of FIG. 14, techniques are provided for efficiently achieving dual-site pacing in the LV lead using a quad-pole LV lead by using either one of both of the LV pulses. In particular, the technique seeks to determine whether it is more efficient to achieve dual-site pacing via one higher energy pulse (LV1) sufficient to achieve concurrent cathodal/anodal capture, as opposed to using two separate lower-energy cathodal-only pulses (LV1, LV2) delivered concurrently. In the example of FIG. 15, techniques are provided for efficiently achieving quad-site pacing in the LV using a quad-pole LV lead. In particular, the technique seeks to determine whether it is more efficient to achieve quad-site pacing using two higher energy pulses (LV1, LV2) each sufficient to achieve concurrent cathodal/anodal capture, as opposed to using two pairs (i.e. four total pulses) of lower-energy cathodal-only pulses delivered in succession.

Beginning with step 700 of FIG. 14, for a selected pair of electrodes of the quad-pole LV lead such as D1 and P4, the pacer/CRT (or external programmer) determines the capture threshold for concurrent anodal/cathodal capture ($CAP_{ANODE/CATHODE}$) using the two electrodes together (D1-P4) and the lower thresholds for cathodal-only capture ($CAP_{CATHODE}$) for each of the two selected electrodes separately as pacing cathodes (e.g. D1-M2 and P4-M3.) For example, automatic capture tests are used to determine $CAP_{ANODE/CATHODE}$ for higher energy LV1 bipolar pulses delivered D1-P4 (i.e. pulses capable of achieving dual-site capture at both D1 and P4.) Another automatic capture test is performed to determine $CAP_{CATHODE}$ for lower energy LV1 bipolar pulses delivered D1-M2 (i.e. pulses capable of achieving single-site cathodal capture at D1.) Another automatic capture test is performed to determine $CAP_{CATHODE}$ for lower energy LV2 bipolar pulses delivered P4-M3 (i.e. pulses capable of achieving single-site cathodal capture at P4.)

At step 702, based on $CAP_{ANODE/CATHODE}$, the device determines the total pulse energy required to achieve dual-site capture within the LV (e.g. at D1 and at P4) using a single simulation pulse (LV1) sufficient to achieve concurrent anodal and cathodal capture using the selected pair of electrodes of the LV lead. This device stores this total pulse energy value as a first energy value. At step 704, based on the $CAP_{CATHODE}$ values, the device determines the total pulse energy required to achieve dual-site capture within the LV using a pair of simulation pulses (LV1 and LV2), each individual pulse sufficient to achieve cathodal-only capture at one of the electrodes of the selected pair (e.g. cathodal-only capture at D1 via D1-M2 and cathodal-only capture at P4 via P4-M3.) The device stores this total pulse energy as a second total energy value.

At step 706, the devices then selects the preferred pacing mode for achieving dual-site capture based on a comparison of the two determined amounts of energy, e.g. either concurrent anodal/cathodal capture with a single pulse delivered D1-P4 or a pair of cathodal-only pulses delivered D1-M2 and P4-M3. Preferably, the device selects the mode requiring the least amount of energy. Hence, if dual-site pacing can be more efficiently achieved at D1 and P4 by delivering one higher energy pulse sufficient to evoke capture at both D1 (cathode) and P4 (anode), then the device would use the concurrent anodal/cathodal pacing mode for achieving dual-site capture. Conversely, if dual-site pacing can be more efficiently achieved at D1 and P4 by delivering two separate lower energy pulses—one delivered D1-M2 and the other delivered P4-M3—(each sufficient only to evoke cathodal capture), then the device would use this cathodal-only pacing mode for achieving dual-site capture since it would use less energy than concurrent anodal/cathodal capture. Still further, the procedure of FIG. 14 can be repeated with different pacing configurations (e.g. D1-M3, P4-M2, etc.) to determine preferred or optimal pacing configurations that minimize required energy or that achieve other desired goals, such as synchronizing contractions better.

FIG. 15 illustrates a technique for achieving quad-site pacing. Some of the steps are similar to those of FIG. 14 and hence will not be described in detail again. Beginning with step 750 of FIG. 15, for both pairs of electrodes of the quad-pole LV lead (such as D1-M2 and M3-P4), the pacer/CRT (or external programmer) determines the capture thresholds for concurrent anodal/cathodal capture ($CAP_{ANODE/CATHODE}$) and the lower thresholds for cathodal-only capture ($CAP_{CATHODE}$) for each of the four electrodes separately. For example, automatic capture tests are used to determine $CAP_{ANODE/CATHODE}$ for higher energy LV1' bipolar pulses delivered D1-M2 (i.e. pulses capable of achieving dual-site capture at both D1 and M2.) Automatic capture tests are also used to determine $CAP_{ANODE/CATHODE}$ for higher energy LV2 bipolar pulses delivered M3-P4 (i.e. pulses capable of achieving dual-site capture at both M3 and P4.) Additional automatic capture tests are performed to determine $CAP_{CATHODE}$ for lower energy bipolar pulses delivered: D1-M2 (i.e. pulses capable of achieving single-site capture at D1); M2-M3 (i.e. pulses capable of achieving single-site capture at M2); M3-P4 (i.e. pulses capable of achieving single-site capture at M3); and P4-M2 (i.e. pulses capable of achieving single-site capture at P4).

At step 752, based on the $CAP_{ANODE/CATHODE}$ values, the device determines the total amount of energy required to achieve quad-site capture within the LV using a pair of concurrent higher voltage simulation pulses (LV1, LV2), each sufficient to achieve anodal and cathodal capture at a respective pair of electrodes of the LV lead (and hence capable of concurrently capturing each of the four sites of the LV lead). This device stores the total pulse energy value determined at step 752 as a first energy value. At step 754, based on the $CAP_{CATHODE}$ values, the device determines the total amount of energy required to achieve quad-site capture within the LV using two pair of lower energy simulation pulses—delivered in succession—each individual pulse sufficient to achieve cathodal-only capture at one of the four electrodes of the LV lead. That is, this second mode uses a first pair of lower energy pulses (LV1/a and LV2/a) to effect capture at two of the four sites, followed by a second pair of lower energy pulses (LV1/b and LV2/b) to effect capture at the other two sites of the four sites. The devices stores the total pulse energy determined at step 754 as a second total energy value.

At step 756, the devices then selects the preferred pacing mode for achieving quad-site capture based on a comparison of the two determined amounts of energy, e.g. either anodal/cathodal capture with two pulses (LV1, LV2) delivered concurrently, or cathodal-only capture with two pairs of pulses (LV1, LV2) delivered in succession. Preferably, the device selects the mode requiring the least amount of energy. Hence, if quad-site pacing can be more efficiently achieved by delivering two higher energy pulses sufficient to evoke capture at all four sites, then the device would use the concurrent anodal/cathodal pacing mode. Conversely, if quad-site pacing can be more efficiently achieved by delivering two separate pairs of lower energy pulses—the two pairs delivered in succession— (each sufficient only to evoke cathodal capture), then the device would use this cathodal-only pacing mode for achieving quad-site capture since it would use less energy than concurrent anodal/cathodal capture. In addition to possibly consuming less energy, the use two higher energy pulses sufficient to evoke anodal and cathodal capture at all four sites concurrently also has the advantage of providing for synchronized pacing. That is, all four sites can be paced concurrently or simultaneously using only two pulses (LV1, LV2), without requiring a second set of pulses to be delivered subject to some timing delay. Note that when using a quad-pole lead, three-site activation may alternatively be exploited, as well as just one or two sites.

Thus, various techniques have been described that exploit and control anodal and cathodal pacing in various implementations. Although primarily described with respect to examples having a CRT with pacing capability (i.e. a CRT-P) and quad-pole LV lead, other implantable medical devices may be equipped to exploit the techniques described herein, such as CRT-D devices as well as standalone pacemakers or ICDs. Depending upon the particular implementation, the techniques described herein may be exploited by the implantable medical device, alone or in combination with a device programmer. For example, the techniques may be performed in accordance with any of the following applications:

An automatic threshold search procedure for 1) concurrent anodal and cathodal capture, 2) cathodal-only capture and 3) complete LOC An automatic, device-based procedure to assess concurrent anodal/cathodal stimulation and adjust pacing amplitude/magnitude (to achieve or to avoid LV anodal stimulation), if necessary, as an extension of existing AUTOCAPTURE™ and CAPCONFIRM™ cathodal algorithms (where CAPCONFIRM™ refers to an ER capture confirmation system provided by St Jude Medical.)

Programmer user interface (UI) to test and document anodal/cathodal stimulation threshold values, above which LV1 and/or LV2 pulse amplitudes should be programmed (where LV1 and LV2 represent pulses to be applied via a quad-pole LV lead using different electrodes of the lead).

Detecting the presence of RV ring anodal capture when cross-chamber pacing is configured to use LV D1 as the cathode and RV ring as the anode. The automatic, device-based procedure can adjust the pacing amplitude or change pacing vector to avoid RV anodal pacing.

For programmer-based implementation where a clinician is responsible for identifying the threshold:
Otherwise conventional capture tests can be started at maximum output or at a value of the physician's choice.

Amplitude is adjusted by the clinician. On the test result screen, the clinician identifies the capture-only threshold and the concurrent anodal/cathodal stimulation threshold.

Alternatively, a separate testing screen can be implemented for anodal stimulation. Pulse amplitude can be decremented from maximum output or incremented from the known or previously measured cathodal-only capture threshold.

Manual versions of these or other capture threshold tests may be implanted as well. In any case, the programmer preferably saves both the upper and lower thresholds for later sessions and review. Pulse amplitude/magnitude can then be selectively programmed to enable or disable concurrent anodal/cathodal capture. Specifically for MSLV, graphic user interface (GUI) objects can be used to indicate whether the programmed amplitude of an MSLV pulse will have anodal stimulation or not.

For device-based automatic systems, the basic procedure and principles used for existing AUTOCAPTURE™ and CAPCONFIRM™ procedures or algorithms may be applied:

The PDI method of ER Detection is preferable but techniques exploiting DMAX may be advantageous too (i.e. the maximum of the rate of change of the ER.)

An Anodal/Cathodal Stimulation Sensitivity Test (similar to existing ER Sensitivity Setup test) may be employed to set the threshold between cathodal-only ER and concurrent anodal/cathodal ER measurements. Because the anodal/cathodal stimulation threshold can be very close to the cathodal-only capture threshold, it is preferable to first identify the cathodal-only capture threshold, then start the anodal/cathodal Sensitivity test from that magnitude. The device increments the pulse amplitude to maximum output while seeking to detect a significant change in ER measurements and while distinguishing anodal stimulation from noise or polarization.

Once a threshold between cathodal-only capture and concurrent anodal/cathodal capture ER measurements has been established, an anodal capture test can be performed. Like the test described just above, pulse magnitude preferably starts at the known cathodal-only capture threshold and increases until a change in ER is detected. The pacing magnitude can then be dynamically adjusted based on measured anodal/cathodal stimulation thresholds and diagnostic trends can be stored.

For the sake of completeness, an exemplary pacer/CRT will now be described, which includes components for performing the functions and steps already described, as well as components for controlling CRT.

Exemplary Pacer/CRT

Figure 16:
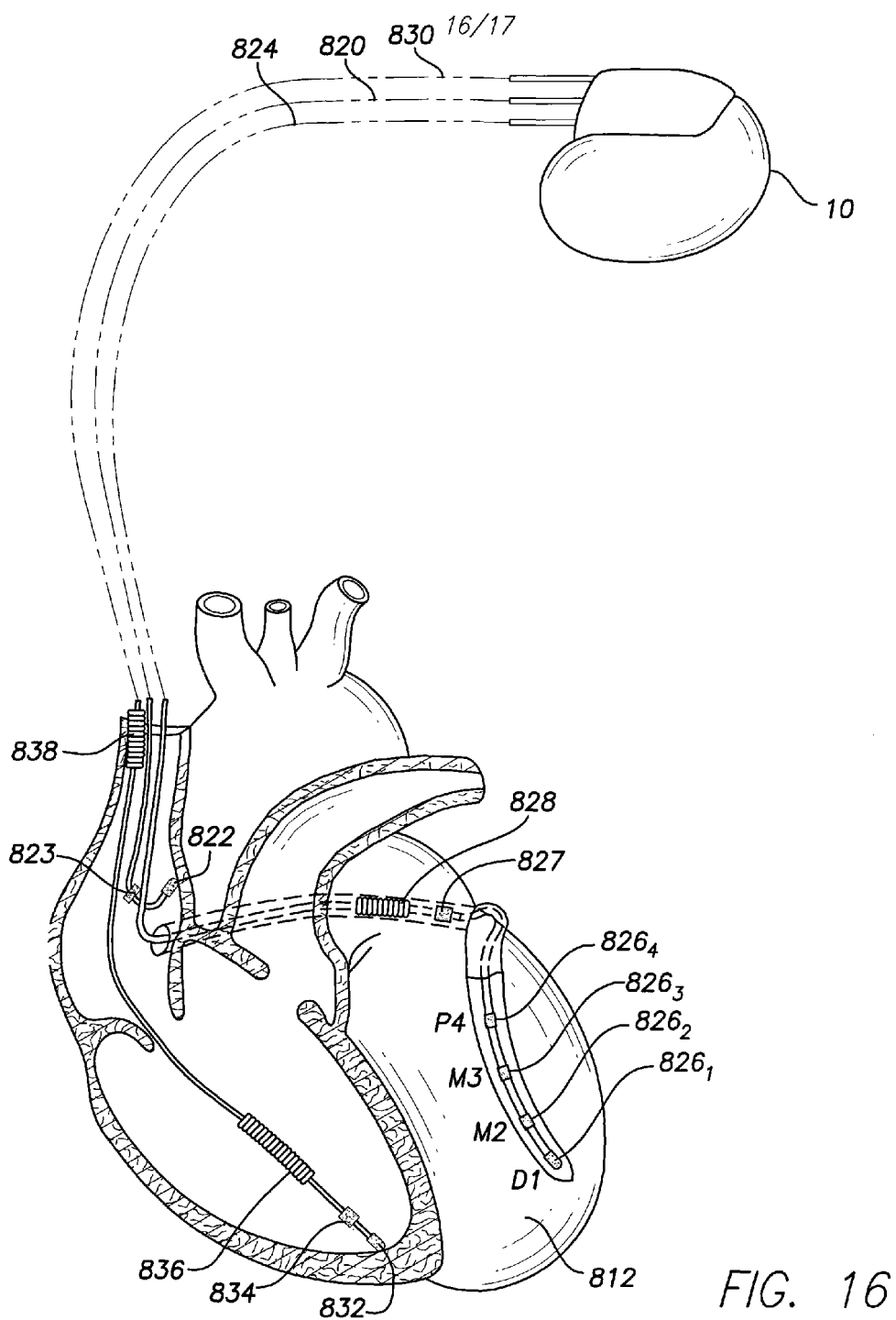
FIG. 16 is a simplified, partly cutaway view, illustrating the device of FIG. 1 along with at set of leads implanted in or on the heart of the patient.
Figure 17:
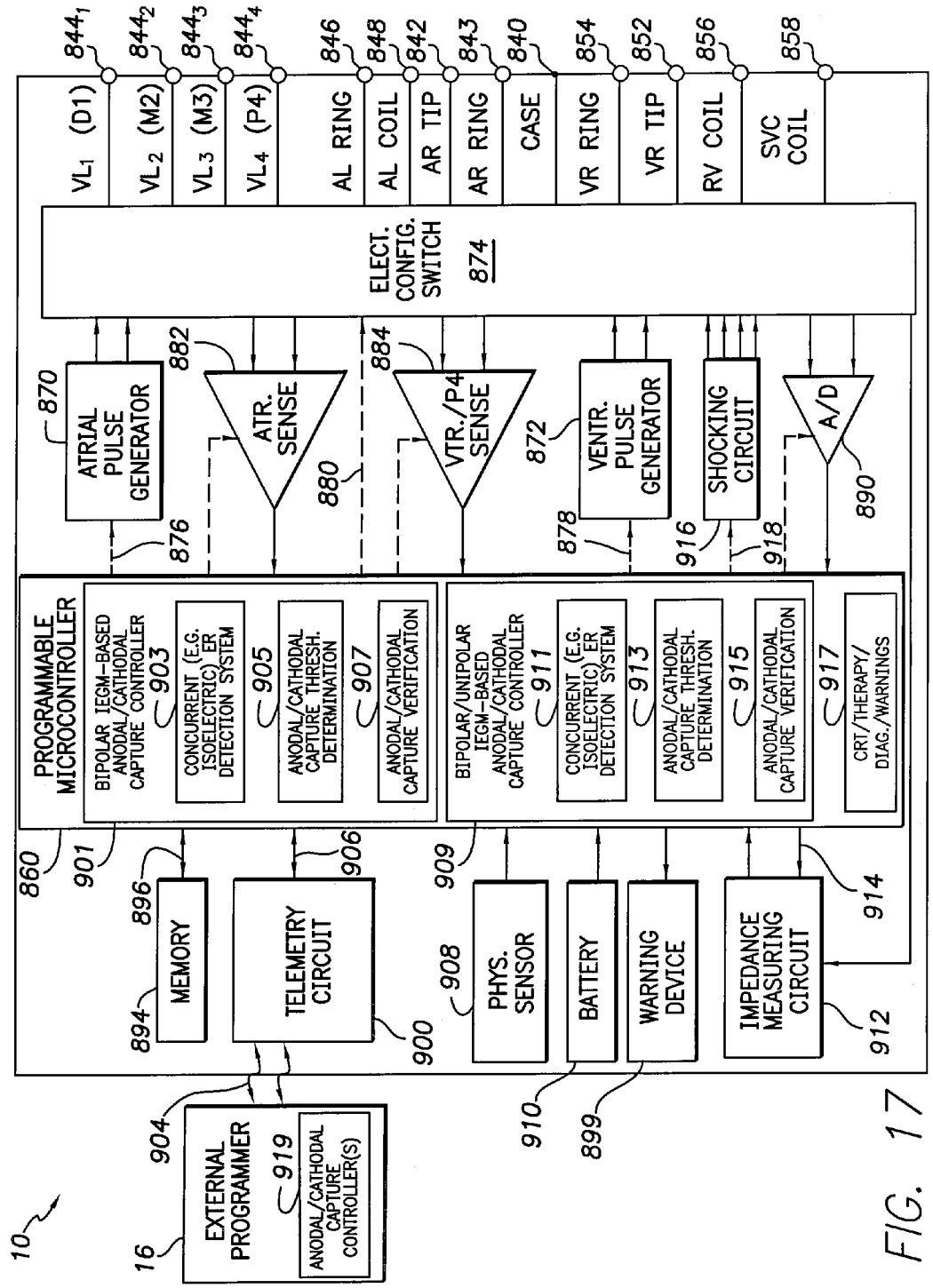
FIG. 17 is a functional block diagram of the pacer/CRT of FIG. 16, illustrating basic circuit elements that provide cardioversion, defibrillation and/or pacing stimulation in the heart and particularly illustrating components for performing the concurrent anodal/cathodal capture assessment and control techniques of FIGS. 2-15.

With reference to FIGS. 16 and 17, a description of an exemplary pacer/CRT will now be provided. FIG. 16 provides a simplified block diagram of the pacer/CRT, which is a dual-chamber stimulation device capable of treating both fast and slow arrhythmias with stimulation therapy, including cardioversion, defibrillation, and pacing stimulation, and also capable of assessing and controlling concurrent anodal/cathodal capture, as discussed above. To provide atrial chamber pacing stimulation and sensing, pacer/CRT 10 is shown in electrical communication with a heart 812 by way of a left atrial lead 820 having an atrial tip electrode 822 and an atrial ring electrode 823 implanted in the atrial appendage. Pacer/CRT 10 is also in electrical communication with the heart by way of a right ventricular lead 830 having, in this embodiment, a ventricular tip electrode 832, a right ventricular ring electrode 834, a right ventricular (RV) coil electrode 836, and a superior vena cava (SVC) coil electrode 838. Typically, the right ventricular lead 830 is transvenously inserted into the heart so as to place the RV coil electrode 836 in the right ventricular apex, and the SVC coil electrode 838 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/CRT 10 is coupled to a multi-pole LV lead 824 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, the exemplary LV lead 824 is designed to receive atrial and ventricular cardiac signals and to deliver left ventricular pacing therapy using a set of four left ventricular electrodes $826_1$ (D1), $826_2$ (M2), $826_3$ (M3), and $826_4$ (P4), left atrial pacing therapy using at least a left atrial ring electrode 827, and shocking therapy using at least a left atrial coil electrode 828. The $826_1$ LV electrode may also be referred to as a "tip" or "distal" LV electrode. The $826_4$ LV electrode may also be referred to as a "proximal" LV electrode. In other examples, more or fewer LV electrodes are provided. Although only three leads are shown in FIG. 16, it should also be understood that additional leads (with one or more pacing, sensing and/or shocking electrodes) might be used and/or additional electrodes might be provided on the leads already shown, such as additional electrodes on the RV lead.

A simplified block diagram of internal components of pacer/CRT 10 is shown in FIG. 17. While a particular pacer/CRT is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 840 for pacer/CRT 10, shown schematically in FIG. 17, is often referred to as the "can", "case" or "case electrode" and may be programmably selected to act as the return electrode for all "unipolar" modes. The housing 840 may further be used as a return electrode alone or in combination with one or more of the coil electrodes, 828, 836 and 838, for shocking purposes. The housing 840 further includes a connector (not shown) having a plurality of terminals, 842, 843, $844_1$-$844_4$, 846, 848, 852, 854, 856 and 858 (shown schematically and, for convenience, the names of the electrodes to which they are connected are shown next to the terminals). As such, to achieve right atrial sensing and pacing, the connector includes at least a right atrial tip terminal ($A_R$ TIP) 842 adapted for connection to the atrial tip electrode 822 and a right atrial ring ($A_R$ RING) electrode 843 adapted for connection to right atrial ring electrode 823. To achieve left chamber sensing, pacing and shocking, the connector includes a left ventricular tip terminal ($VL_1$ (D1)) $844_1$ and additional LV electrode terminals $844_2$-$844_4$ for the other LV electrodes of the LV lead.

The connector also includes a left atrial ring terminal ($A_L$ RING) 846 and a left atrial shocking terminal ($A_L$ COIL) 848, which are adapted for connection to the left atrial ring electrode 827 and the left atrial coil electrode 828, respectively. To support right chamber sensing, pacing and shocking, the connector further includes a right ventricular tip terminal ($V_R$ TIP) 852, a right ventricular ring terminal (V$_R$ RING) 854, a right ventricular shocking terminal (RV COIL) 856, and an SVC shocking terminal (SVC COIL) 858, which are adapted for connection to the right ventricular tip electrode 832, right ventricular ring electrode 834, the V$_R$ coil electrode 836, and the SVC coil electrode 838, respectively.

At the core of pacer/CRT 10 is a programmable microcontroller 860, which controls the various modes of stimulation therapy. As is well known in the art, the microcontroller 860 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 860 includes the ability to process or monitor input signals (data) as controlled by a program code stored in a designated block of memory. The details of the design and operation of the microcontroller 860 are not critical to the invention. Rather, any suitable microcontroller 860 may be used that carries out the functions described herein. The use of microprocessor-based control circuits for performing timing and data analysis functions are well known in the art.

As shown in FIG. 17, an atrial pulse generator 870 and a ventricular pulse generator 872 generate pacing stimulation pulses for delivery by the right atrial lead 820, the right ventricular lead 830, and/or the LV lead 824 via an electrode configuration switch 874. It is understood that in order to provide stimulation therapy in each of the four chambers of the heart, the atrial and ventricular pulse generators, 870 and 872, may include dedicated, independent pulse generators, multiplexed pulse generators or shared pulse generators. The pulse generators, 870 and 872, are controlled by the microcontroller 860 via appropriate control signals, 876 and 878, respectively, to trigger or inhibit the stimulation pulses.

The microcontroller 860 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 874 includes a plurality of switches for connecting the desired electrodes to the appropriate I/O circuits, thereby providing complete electrode programmability. Accordingly, the switch 874, in response to a control signal 880 from the microcontroller 860, determines the polarity of the stimulation pulses (e.g., unipolar, bipolar, combipolar, etc.) by selectively closing the appropriate combination of switches (not shown) as is known in the art. The switch also switches among the various LV electrodes.

Atrial sensing circuits 882 and ventricular sensing circuits 884 may also be selectively coupled to the right atrial lead 820, LV lead 824, and the right ventricular lead 830, through the switch 874 for detecting the presence of cardiac activity in each of the four chambers of the heart. Accordingly, the atrial and ventricular sensing circuits, 882 and 884, may include dedicated sense amplifiers, multiplexed amplifiers or shared amplifiers. The switch 874 determines the "sensing polarity" of the cardiac signal by selectively closing the appropriate switches, as is also known in the art. In this way, the clinician may program the sensing polarity independent of the stimulation polarity. Each sensing circuit, 882 and 884, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/CRT 10 to deal effectively with the difficult problem of sensing the low amplitude signal characteristics of atrial or ventricular fibrillation. The outputs of the atrial and ventricular sensing circuits, 882 and 884, are connected to the microcontroller 860 which, in turn, are able to trigger or inhibit the atrial and ventricular pulse generators, 870 and 872, respectively, in a demand fashion in response to the absence or presence of cardiac activity in the appropriate chambers of the heart.

For arrhythmia detection, pacer/CRT 10 utilizes the atrial and ventricular sensing circuits, 882 and 884, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 860 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 890. The data acquisition system 890 is configured to acquire intracardiac electrogram signals, convert the raw analog data into a digital signal, and store the digital signals for later processing and/or telemetric transmission to an external device 16. The data acquisition system 890 is coupled to the right atrial lead 820, the LV lead 824, and the right ventricular lead 830 through the switch 874 to sample cardiac signals across any pair of desired electrodes. The microcontroller 860 is further coupled to a memory 894 by a suitable data/address bus 896, wherein the programmable operating parameters used by the microcontroller 860 are stored and modified, as required, in order to customize the operation of pacer/CRT 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/CRT 10 may be non-invasively programmed into the memory 894 through a telemetry circuit 900 in telemetric communication with the external device 16, such as a programmer, transtelephonic transceiver or a diagnostic system analyzer. The telemetry circuit 900 is activated by the microcontroller by a control signal 906. The telemetry circuit 900 advantageously allows intracardiac electrograms and status information relating to the operation of pacer/CRT 9 (as contained in the microcontroller 860 or memory 894) to be sent to the external device 16 through an established communication link 904. Pacer/CRT 10 further includes an accelerometer or other physiologic sensor 908, commonly referred to as a "rate-responsive" sensor because it is typically used to adjust pacing stimulation rate according to the exercise state of the patient. However, the physiological sensor 908 may further be used to detect changes in cardiac output, changes in the physiological condition of the heart, or diurnal changes in activity (e.g., detecting sleep and wake states) and to detect arousal from sleep. Accordingly, the microcontroller 860 responds by adjusting the various pacing parameters (such as rate, AV delay, VV delay, etc.) at which the atrial and ventricular pulse generators, 870 and 872, generate stimulation pulses. While shown as being included within pacer/CRT 10, it is to be understood that the physiologic sensor 908 may also be external to pacer/CRT 10, yet still be implanted within or carried by the patient. A common type of rate responsive sensor is an activity sensor incorporating an accelerometer or a piezoelectric crystal, which is mounted within the housing 840 of pacer/CRT 10. Other types of physiologic sensors are also known, for example, sensors that sense the oxygen content of blood, respiration rate and/or minute ventilation, pH of blood, ventricular gradient, etc.

The pacer/CRT additionally includes a battery 910, which provides operating power to all of the circuits shown in FIG. 17. The battery 910 may vary depending on the capabilities of pacer/CRT 10. If the system only provides low voltage therapy, a lithium iodine or lithium copper fluoride cell typically may be utilized. For pacer/CRT 10, which employs shocking therapy, the battery 910 should be capable of operating at low current drains for long periods, and then be capable of providing high-current pulses (for capacitor charging) when the patient requires a shock pulse. The battery 910 should also have a predictable discharge characteristic so that elective replacement time can be detected. Accordingly, appropriate batteries are employed.

As further shown in FIG. 17, pacer/CRT 10 is shown as having an impedance measuring circuit 912, which is enabled by the microcontroller 860 via a control signal 914. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, and detecting cardiogenic impedance, etc. The impedance measuring circuit 912 is advantageously coupled to the switch 874 so that any desired electrode may be used.

In the case where pacer/CRT 10 is intended to operate as an ICD device, it detects the occurrence of an arrhythmia, and automatically applies an appropriate electrical shock therapy to the heart aimed at terminating the detected arrhythmia. To this end, the microcontroller 860 further controls a shocking circuit 916 by way of a control signal 918. The shocking circuit 916 generates shocking pulses of low (up to 0.5 joules), moderate (0.5-9 joules) or high energy (11 to 40 joules or more), as controlled by the microcontroller 860. Such shocking pulses are applied to the heart of the patient through at least two shocking electrodes, and as shown in this embodiment, selected from the left atrial coil electrode 828, the RV coil electrode 836, and/or the SVC coil electrode 838. The housing 840 may act as an active electrode in combination with the RV electrode 836, or as part of a split electrical vector using the SVC coil electrode 838 or the left atrial coil electrode 828 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 8-40 joules or more), delivered asynchronously (since R-waves may be too disorganized), and pertaining exclusively to the treatment of fibrillation. Accordingly, the microcontroller 860 is capable of controlling synchronous or asynchronous delivery of shocking pulses.

An internal warning device 899 may be provided for generating perceptible warning signals to the patient via vibration, voltage or other methods.

Insofar as concurrent anodal/cathodal capture is concerned, the microcontroller includes a bipolar IEGM-based concurrent anodal/cathodal capture controller 901 operative to assess and control concurrent anodal/cathodal capture based on bipolar IEGM signals. Bipolar controller 901 includes, in this example, concurrent ER detection system 903 operative to detect an indication of isoelectric (or other) ERs representative of anodal and cathodal capture. The controller also includes a concurrent anodal/cathodal capture detection system 905 operative to determine the anodal/cathodal capture threshold sufficient to achieve both anodal and cathodal capture from the indication within the bipolar IEGM signals of ERs and to set pulse magnitudes, accordingly, in accordance with the bipolar techniques discussed above in connection with FIGS. 4-6. The exemplary bipolar controller 901 also includes, in this example, a concurrent anodal/cathodal capture verification system 907 operative to verify concurrent anodal/cathodal capture in accordance with the bipolar techniques discussed above in connection with FIG. 7.

The microcontroller also includes a bipolar/unipolar IEGM-based concurrent anodal/cathodal capture controller 909 operative to assess and control concurrent anodal/cathodal capture based on bipolar and unipolar IEGM signals. Bipolar/unipolar controller 909 includes, in this example, a concurrent ER detection system 911 operative to detect the indication of isoelectric (or other) ERs within the bipolar IEGM representative of concurrent anodal and cathodal capture. The controller also includes a concurrent anodal/cathodal capture detection system 913 operative to analyze bipolar and unipolar IEGM signals to detect an anodal/cathodal capture threshold sufficient to achieve concurrent anodal and cathodal capture in accordance with techniques discussed above in connection with FIGS. 9-11. The exemplary bipolar/unipolar controller 909 also includes, in this example, a concurrent anodal/cathodal capture verification system 915 operative to verify concurrent anodal/cathodal capture in accordance with the bipolar/unipolar techniques discussed above in connection with FIG. 12.

Therapy, diagnostics and warnings are controlled by system 917, which also controls delivery of CRT, where appropriate.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like. As noted, at least some of the techniques described herein can be performed by (or under the control of) an external device, such as programmer 16. A concurrent anodal/cathodal capture controller 919 is shown as a component of the external device, which may control or perform all or some of the functions described herein based on signals and data received from the pacer/CRT. Controller 919 may include components corresponding to components 901 and 909 of the microcontroller of the pacer/CRT.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use with an implantable medical device equipped for bipolar electrical stimulation and sensing of heart tissues using cardiac electrodes, the method comprising:
   delivering bipolar stimulus using a pair of the cardiac electrodes while sensing bipolar intracardiac electrogram (IEGM) signals using the pair of the cardiac electrodes;
   detecting an indication within the bipolar IEGM signals of evoked responses (ERs) representative of anodal capture within myocardial tissues associated with using the anode of the pair of the cardiac electrodes and cathodal capture within myocardial tissues associated with using the cathode of the pair of the cardiac electrodes;
   determining an anodal/cathodal capture threshold sufficient to achieve both anodal and cathodal capture from the indication within the bipolar IEGM signals of the ERs; and
   setting a magnitude for subsequent bipolar stimulus above the anodal/cathodal capture threshold to enable concurrent anodal and cathodal capture with a single stimulus pulse.

2. The method of claim 1 further including analyzing subsequent bipolar IEGM signals to confirm the concurrent anodal and cathodal capture during subsequent bipolar stimulation by detecting additional ERs representative of the anodal and cathodal capture.

3. The method of claim 1 wherein the magnitude for subsequent bipolar stimulus is set below the anodal/cathodal capture threshold to disable anodal capture.

4. The method of claim 1 wherein the detecting an indication within the bipolar IEGM signals of ERs includes:
   incrementing a magnitude of the bipolar stimulus while detecting the ERs within the bipolar IEGM signals;
   detecting a stimulus magnitude above which the ERs within the bipolar IEGM signals decrease from a high ER associated with cathodal-only capture to a low ER associated with the concurrent anodal and cathodal capture.

5. The method of claim 4 wherein, if unable to detect the indication within the bipolar IEGM signals of ERs representative of the concurrent anodal and cathodal capture within a predetermined range of acceptable stimulus magnitudes, repeating the delivering and detecting with another bipolar pair of electrodes.

6. The method of claim 1 wherein the detecting an indication within the bipolar IEGM signals of ERs includes:
   decrementing a magnitude of the bipolar stimulus from a maximum permissible magnitude while detecting the ERs within the bipolar IEGM signals;
   detecting a stimulus magnitude below which the ERs within the bipolar IEGM signals increase from a low ER associated with the concurrent anodal and cathodal capture to a high ER associated with cathodal-only capture.

7. The method of claim 1 further comprising analyzing the bipolar IEGM signals to additionally detect a cathodal-only capture threshold sufficient to achieve the cathodal capture without the anodal capture.

8. The method of claim 7 wherein a magnitude for subsequent stimulus is set above the cathodal-only capture threshold but below the anodal/cathodal capture threshold to achieve cathodal-only capture.

9. The method of claim 1 further including:
   sensing unipolar IEGM signals using one of the pair of the cardiac electrodes as a cathode and a device housing electrode as an anode while the bipolar stimulus is delivered; and
   comparing the bipolar IEGM signals to the unipolar IEGM signals to detect the anodal/cathodal capture threshold.

10. The method of claim 1 further including:
    sensing unipolar IEGM signals using one of the pair of the cardiac electrodes as a cathode and a device housing electrode as an anode while the bipolar stimulus is delivered; and
    comparing the bipolar IEGM signals to the unipolar IEGM signals to confirm the concurrent anodal and cathodal capture during subsequent stimulation.

11. The method of claim 10 wherein confirming the concurrent anodal and cathodal capture during subsequent stimulus includes:
    comparing the bipolar IEGM signals associated with stimulus pulses delivered above the anodal/cathodal capture threshold with corresponding unipolar IEGM signals; and
    confirming that the unipolar IEGM signals exhibit greater ERs than the bipolar IEGM signals as expected with the concurrent anodal and cathodal capture.

12. The method of claim 1 for use with an implantable medical device equipped with a multi-polar left ventricular (LV) lead and further comprising:
    determining a first amount of energy required to achieve dual-site capture within the left ventricle using a single simulation pulse sufficient to achieve the concurrent anodal and cathodal capture using a selected pair of electrodes of the LV lead;
    determining a second amount of energy required to achieve dual-site capture within the left ventricle using a pair of simulation pulses, each individual pulse sufficient to achieve cathodal-only capture at a respective one of the selected pair of electrodes of the LV lead; and
    selecting a pacing mode for achieving the dual-site capture based on a comparison of the first and second amounts of energy.

13. The method of claim 1 for use with an implantable medical device equipped with a quad-polar left ventricular (LV) lead wherein separate anodal/cathodal capture thresholds are determined for two separate pairs of electrodes of the LV lead.

14. The method of claim 13 further comprising:
    determining a first amount of energy required to achieve quad-site capture within the left ventricle using a pair of simulation pulses, each sufficient to achieve the concurrent anodal and cathodal capture at a respective pair of electrodes of the LV lead;
    determining a second amount of energy required to achieve quad-site capture within the left ventricle using two pair of simulation pulses, delivered in succession, each individual pulse sufficient to achieve cathodal-only capture at one of the electrodes of the LV lead; and
    selecting a pacing mode for achieving the quad-site capture based on a comparison of the first and second amounts of energy.

15. The method of claim 1 wherein the delivering, detecting, and determining are performed by the implantable medical device.

16. The method of claim 1 wherein at least some of the delivering, detecting, and determining are performed by an external device in communication with the implantable medical device.

17. The method of claim 1 wherein the bipolar stimulus comprises any stimulus wherein both an anodal electrode and a cathodal electrode of the pair of the cardiac electrodes are implanted on or within a heart.

18. The method of claim 17 wherein the bipolar stimulus includes single chamber stimulus wherein both the anodal electrode and the cathodal electrode are implanted on or within a same chamber of the heart.

19. The method of claim 17 wherein the bipolar stimulus includes cross-chamber stimulus wherein the anodal electrode and the cathodal electrode are implanted on or within different chambers of the heart.

20. The method of claim 1 wherein the detecting an indication within the bipolar IEGM signals of ERs representative of the anodal and cathodal capture is performed to detect an indication of concurrent ERs.

21. A system for use with an implantable medical device equipped for bipolar electrical stimulation and sensing of heart tissues using cardiac electrodes, the system comprising:
 a bipolar stimulus controller operative to control delivery of bipolar stimulus using a pair of cardiac electrodes while sensing bipolar intracardiac electrogram (IEGM) signals using the pair of cardiac electrodes;
 an evoked response (ER) detection system operative to detect an indication within the bipolar IEGM signals of ERs representative of anodal capture within myocardial tissues associated with using the anode of the pair of cardiac electrodes and cathodal capture within myocardial tissues associated with using the cathode of the electrode pair of cardiac electrodes;
 an anodal/cathodal capture threshold determination system operative to determine the anodal/cathodal capture threshold sufficient to achieve both anodal and cathodal capture from the indication within the bipolar IEGM signals of the ERs; and
 an anodal/cathodal stimulus controller operative to set a magnitude for subsequent stimulus to selectively enable concurrent anodal and cathodal capture with a single stimulation pulse.

22. A system for use with an implantable medical device equipped for bipolar electrical stimulation and sensing of heart tissues using cardiac electrodes, the system comprising:
 means for delivering bipolar stimulus using a pair of the cardiac electrodes while sensing bipolar intracardiac electrogram (IEGM) signals using the pair of the cardiac electrodes;
 means for detecting an indication within the bipolar IEGM signals of evoked responses (ERs) representative of anodal capture within myocardial tissues associated with using the anode of the pair of the cardiac electrodes and cathodal capture within myocardial tissues associated with using the cathode of the pair of the cardiac electrodes;
 means for determining an anodal/cathodal capture threshold sufficient to achieve concurrent anodal and cathodal capture from a single stimulation pulse, from the indication within the bipolar IEGM signals of the ERs.

* * * * *